(12) United States Patent
Kunio

(10) Patent No.: US 10,842,589 B2
(45) Date of Patent: Nov. 24, 2020

(54) METHOD FOR DISPLAYING AN ANATOMICAL IMAGE OF A CORONARY ARTERY ON A GRAPHICAL USER INTERFACE

(71) Applicant: Canon U.S.A., Inc., Melville, NY (US)

(72) Inventor: Mie Kunio, Boston, MA (US)

(73) Assignee: Canon U.S.A., Inc., Melville, NY (US)

( * ) Notice: Subject to any disclaimer, the term of this patent is extended or adjusted under 35 U.S.C. 154(b) by 361 days.

(21) Appl. No.: 15/923,956

(22) Filed: Mar. 16, 2018

(65) Prior Publication Data

US 2018/0271614 A1 Sep. 27, 2018

Related U.S. Application Data

(60) Provisional application No. 62/474,248, filed on Mar. 21, 2017.

(51) Int. Cl.
*A61B 90/00* (2016.01)
*A61B 6/12* (2006.01)
(Continued)

(52) U.S. Cl.
CPC ............ *A61B 90/37* (2016.02); *A61B 5/0084* (2013.01); *A61B 5/743* (2013.01); *A61B 6/12* (2013.01);
(Continued)

(58) Field of Classification Search
CPC ....... A61B 90/37; A61B 34/20; A61B 5/0084; A61B 6/12
See application file for complete search history.

(56) References Cited

U.S. PATENT DOCUMENTS 4,397,317 A * 8/1983 Villa-Real .......... A61B 5/02208
600/493
5,357,550 A 10/1994 Asahina et al.
(Continued)

FOREIGN PATENT DOCUMENTS

| JP | 2013-56113 A | 3/2013 |
| WO | 2014/175853 A1 | 10/2014 |
| WO | 2015/045368 A1 | 4/2015 |

OTHER PUBLICATIONS

Athanasiou, L.S., et al., "3D Reconstruction of Coronay Arteries using Frequency Domain Optical Coherence Tomography Images and Biplane Angiography", IEEE, Aug. 2012 (four pages).
(Continued)

*Primary Examiner* — Santiago Garcia
(74) *Attorney, Agent, or Firm* — Canon U.S.A., Inc. I.P. Division

(57) ABSTRACT

A method for displaying an anatomical image of a coronary artery on a graphical user interface with information acquired from a plurality of intravascular image frames. The method may include detecting qualitative information from the plurality of intravascular image frames, creating one or more indicator(s) from the qualitative information detected, and determining a spatial relationship between the anatomical image and a plurality of acquisition locations of the plurality of intravascular image frames and generating its linear representation. The method also includes displaying the anatomical image of the coronary artery with the linear representation overlaid thereon on a display device and overlaying the one or more indicator(s) representing at least one type of qualitative information on the anatomical image along the linear representation.

29 Claims, 23 Drawing Sheets

(51) Int. Cl.
| | |
|---|---|
| *A61B 34/20* | (2016.01) |
| *A61B 5/00* | (2006.01) |
| *A61B 17/00* | (2006.01) |
| *A61F 2/82* | (2013.01) |
| *A61B 6/00* | (2006.01) |
| *A61B 17/3207* | (2006.01) |

(52) U.S. Cl.
CPC ........ *A61B 6/504* (2013.01); *A61B 17/32075* (2013.01); *A61B 34/20* (2016.02); *A61B 5/0066* (2013.01); *A61B 6/481* (2013.01); *A61B 2017/00199* (2013.01); *A61B 2017/00292* (2013.01); *A61B 2034/2065* (2016.02); *A61B 2090/364* (2016.02); *A61B 2090/372* (2016.02); *A61B 2090/376* (2016.02); *A61B 2090/3735* (2016.02); *A61F 2/82* (2013.01)

(56) References Cited

U.S. PATENT DOCUMENTS

| | | | |
|---|---|---|---|
| 6,565,514 B2 | 5/2003 | Svanerudh et al. | |
| 6,763,261 B2 | 7/2004 | Casscells, III et al. | |
| 7,292,715 B2 | 11/2007 | Furnish | |
| 7,414,779 B2 | 8/2008 | Huber et al. | |
| 7,916,387 B2 | 3/2011 | Schmitt | |
| 7,978,916 B2 | 7/2011 | Klingensmith et al. | |
| 8,175,684 B2 | 5/2012 | Vaillant et al. | |
| 8,315,282 B2 | 11/2012 | Huber et al. | |
| 8,325,419 B2 | 12/2012 | Schmitt | |
| 8,412,312 B2 | 4/2013 | Judell et al. | |
| 8,478,387 B2 | 7/2013 | Xu | |
| 8,565,859 B2 | 10/2013 | Wang et al. | |
| 8,581,643 B1 | 11/2013 | Schmitt | |
| 8,909,323 B2 | 12/2014 | Baumgart | |
| RE45,534 E | 6/2015 | Huennekens et al. | |
| 9,121,926 B2 | 9/2015 | Nair et al. | |
| 9,138,147 B2 | 9/2015 | Schmitt et al. | |
| 9,286,673 B2 | 3/2016 | Begin et al. | |
| 9,292,918 B2 | 3/2016 | Zagrodsky et al. | |
| 9,295,450 B2 | 3/2016 | Furuichi et al. | |
| 9,301,687 B2 * | 4/2016 | Kemp | A61B 5/6852 |
| 9,307,926 B2 | 4/2016 | Begin et al. | |
| 9,351,698 B2 | 5/2016 | Dascal et al. | |
| 9,462,950 B2 | 10/2016 | Xu | |
| 9,833,221 B2 | 12/2017 | Hutchins et al. | |
| 9,901,317 B2 | 2/2018 | Shimamura et al. | |
| 2010/0208957 A1 | 8/2010 | Chen et al. | |
| 2014/0276011 A1* | 9/2014 | Schmitt | A61B 5/02007 600/425 |
| 2015/0131886 A1* | 5/2015 | Aben | A61B 8/5261 382/132 |
| 2015/0250438 A1 | 9/2015 | Bozkaya et al. | |
| 2015/0272442 A1 | 10/2015 | Motafakker-Fard et al. | |
| 2016/0171711 A1 | 6/2016 | Gopinath et al. | |
| 2016/0196666 A1* | 7/2016 | Venkatraghavan | G06T 7/254 382/130 |
| 2016/0206267 A1* | 7/2016 | Shimizu | A61B 6/12 |
| 2016/0314246 A1* | 10/2016 | Roberge | G16H 10/60 |
| 2016/0335766 A1* | 11/2016 | Ambwani | G06K 9/4647 |
| 2017/0020392 A1 | 1/2017 | Xu | |
| 2017/0024532 A1* | 1/2017 | Gopinath | G16H 50/20 |
| 2017/0181701 A1* | 6/2017 | Fehrenbacher | A61B 17/29 |
| 2017/0281114 A1* | 10/2017 | Riddell | G06T 7/0012 |
| 2017/0296055 A1* | 10/2017 | Gardner | G01N 21/314 |
| 2017/0367678 A1* | 12/2017 | Sirtori | G16H 50/30 |
| 2017/0367768 A1* | 12/2017 | Zarkh | A61M 25/09 |
| 2020/0037982 A1* | 2/2020 | Van Der Horst | A61B 5/061 |

OTHER PUBLICATIONS

Blondel, C., et al., "Reconstruction of Coronary Arteries From a Single Rotational X-Ray Projection Sequence", IEEE Transactions on Medical Imaging, vol. 25, No. 5, May 2006, pp. 653-663.

Bourantas, C. V., et al., "A new methodology for accurate 3-dimensional coronary artery reconstruction using routine intravascular ultrasound and angiographic data: implications for widespread assessment of endothelial shear stress in humans", Euro Intervention, vol. 9, Apr. 2013, pp. 582-593.

Bourantas, C. V., et al., "ANGIOCARE: An Automated System for Fast Three-Dimesional Coronary Reconstruction by Integrating Angiographic and Intracoronay Ultrasound Data", Catheterization and Cardiovascular Intervention, vol. 72, Apr. 2008, pp. 166-175.

Bourantas, C. V., et al., "Bioresorbable vascular scaffold treatment induces the formation of neointimal cap that seals the underlying plaque without compromising the luminal dimensions: a concept based on serial optical coherence tomography data", Euro Intervention, Oct. 2014, pp. 1-16.

Bourantas, C.V., et al., "A method for 3D reconstruction of coronary arteries using biplane angiography and intravascular ultrasound images", Computerized Medical Imaging and Graphics, vol. 29, Nov. 2005, pp. 597-606.

Cardenes, R., et al., "3D Reconstruction of Coronary Arteries From Rotational X-Ray Angiography", IEEE, May 2012, pp. 618-621.

Coskun, A. U., et al., "Reproducibility of Coronary Lumen, Plaque, and Vessel Wall Reconstruction and of Endothelial Shear Stress Measurements In Vivo in Humans", Catheterization and Cardiovascular Interventions, vol. 30, Sep. 2003, pp. 67-78.

Dehkordi, et al., "Extraction of the Best Frames in Coronary Angiograms for Diagnosis and Analysis", J Med Signals, Sens., vol. 6, No. 3, Jul.-Sep. 2016, pp. 150-157 (14 pages included with figures).

Ellwein, L.M., et al., Optical Coherence Tomography for Patient-specific 3D Artery Reconstruction and Evaluation of Wall Shear Stress in a Left Circumflex Coronary Artery, Cardiovascular Engineering and Technology, vol. 2, No. 3, Sep. 2011, pp. 212-227.

Giannoglou, G. D., et al., "In-vivo validation of spatially correct three-dimensional reconstruction of human coronary arteries by integrating intravascular ultrasound and biplane angiography", Diagnostic methods, vol. 17, No. 6, Sep. 2006, pp. 533-543.

Hebsgaard, L., et al., "Co-registration of optical coherence tomography and X-ray angiography in percutaneous coronary intervention. The Does Optical Coherence Tomography Optimize Revascularization (DOCTOR) fusion study", International Journal of Cardiology, vol. 182, Mar. 2015, pp. 272-278.

Hoffmann, K. R., et al., "Biplane X-ray angiograms, intravascular ultrasound, and 3D visualization of coronary vessels", International Journal of Cardiac Imaging, vol. 15, Dec. 1999, pp. 495-512.

Kang, D., et al., "Three-Dimensional Blood Vessel Quantification via Centerline Deformation", IEEE Transations on Medical Imaging, vol. 28, No. 3, Mar. 2009, pp. 405-414.

Khaleel, H. H., et al., "A Review paper of 3D Surface Reconstruction of Coronary Arteries From Cardiovascular Angiography", 2012 International Conference on Advanced Computer Science Applications and Technologies (Acsat), pp. 419-435, Nov. 2012, DOI: Doi 10.1109/Acsat.2012.13.

Klein, H. M., et al., "3D-Surface Reconstruction of Intravascular Ultrasound Images Using Personal Computer Hardware and a Motorized Catheter Control", Cardiovascular Interventional Radiology, vol. 15, Mar.-Apr. 1992, pp. 97-101.

Kraus, M.F., et al., "Motion correction in optical coherence tomography volumes on a per A-scan basis using orthogonal scan patterns", Bio. Med. Express, vol. 3, No. 6, Jun. 1, 2012, pp. 1182-1199.

Kumar, R.P., et al., "3D multiscale vessel enhancement based centerline extraction of blood vessels", Medical Imaging 2013: Image Processing, Proc. SPIE vol. 8669, Mar. 2013 (ten pages).

Laban, M., et al., "ANGUS: A New Approach to Three-Dimensional Reconstruction of Coronary Vessels by Combined Use of Angiography and Intravascular Ultrasound", Computers in Cardiology, IEEE, Oct. 1995, pp. 325-238.

Li, Y., et al., "Impact of Side Branch Modeling on Computation of Endothelial Shear Stress in Coronary Artery Disease: Coronary Tree Reconstruction by Fusion of 3D Angiography and OCT", Journal of the American College of Cardiology, vol. 66, Issue No. 2, Jul. 2015, pp. 125-135.

(56) References Cited

OTHER PUBLICATIONS

Maehara, et al., "Assessment and Quantification of Stent Results by Intracoronary Optical Coherence Tomography", Intervent. Cardiol. Clin., vol. 4, Issue 3, Jul. 2015, pp. 285-294.
Oubel, et al., "Analysis of Intracranial Aneurysm Wall Motion and its Effects on Hemodynamic Patterns", Proc. SPIE, Medical Imaging, vol. 6511, Mar. 2007 (eight pages included).
Prati, et al., "Clinical Impact of OCT Findings During PCI: The CLI-OPCI II Study", JACC: Cardiovascular Imaging, vol. 8, No. 11, Nov. 2015, pp. 1297-1305.
Reiber, J., et al., "QCA, IVUS and OCT in interventional cardiology in 2011", Cardiovascular Diagnosis and Therapy, vol. 1, No. 1, Dec. 2011, pp. 57-70.
Rivest-Hénault, D., et al., "Nonrigid 2D/3D Registration of Coronary Artery Models With Live Fluoroscopy for Guidance of Cardiac Interventions", IEEE Transations on Medical Imaging, vol. 31, No. 8, Aug. 2012, pp. 1557-1572.
Sarwal, A., et al., "Three dimensional reconstruction of coronary arteries from two views", Computer Methods and Programs in Biomedicine, vol. 65, Issue 1, Jan. 2001, pp. 25-43, ISSN: 0169-2607.
Shekhar, R., et al., "Fusion of Intravascular Ultrasound and Biplane Angiography for Three-Dimensional Reconstruction of Coronary Arteries", IEEE, Computers in Cardiology, Sep. 1996, pp. 5-8.
Slager, C. J., et al., "True 3-Dimensional Reconstruction of Coronary Arteries in Patients by Fusion of Angiography and IVUS (ANGUS) and Its Quantitative Validation", vol. 102, No. 5, Aug. 2000, pp. 511-516.
Subramanian, K. R., et al., "Accurate 3D reconstruction of complex blood vessel geometries from intravascular ultrasound images: in vitro study", Journal of Medical Engineering & Technology, vol. 24, No. 4, Jul./Aug. 2000, pp. 131-140.
Timmins, L. H., et al., "Framework to Co-register Longitudinal Virtual Histology-Intravascular Ultrasound Data in the Circumferential Direction", IEEE Transactions on Medical Imaging, vol. 32, No. 11, Nov. 2013, pp. 1989-1996.
Tu, S., et al., "Fusion of 3D QCA and IVUS/OCT", International Journal of Cardiovascular Imaging, vol. 27, Issue 2, Feb. 2011, pp. 197-207.
Tu, S., et al., "Assessment of obstruction length and optimal viewing angle from biplane X-ray angiograms", Int. J. Cardiovasc. Imaging, vol. 26, No. 1, Jan. 2010, pp. 5-17.
Tu, S., et al., "In vivo comparison of arterial lumen dimensions assessed by co-registered three-dimensional (3D) quantitative coronary angiography, intravascular ultrasound and optical coherence tomography", Int. J. Cardiovasc. Imaging, vol. 28, No. 6, Aug. 2012, pp. 1315-1327.
Tu, S., et al., "In Vivo Flow Simulation at Coronary Bifurcation Reconstructed by Fusion of 3-Dimensional X-ray Angiography and Optical Coherence Tomography", Circ. Cardiovasc. Interv., vol. 6, No. 2, Apr. 2013, pp. e15-e17 (5 pages included).
Van Der Giessen, A., et al., "3D fusion of intravascular ultrasound and coronary computed tomography for in-vivo wall shear stress analysis: a feasibility study", Int. J. Cardiovasc. Imaging, vol. 26, No. 7, Oct. 2010, pp. 781-796.
Wahle, A., et al., "Fusion of Angiography and Intravascular Ultrasound in vivo: Establishing the Absolute 3-D Frame Orientation", IEEE Transations on Biomedical Engineering, vol. 46, No. 10, Oct. 1999, pp. 1176-1180.
Wahle, A., et al., "Geometrically Correct 3-D Reconstruction of Intravascular Ultrasound Images by Fusion with Biplane Angiography—Methods and Validation", IEEE Transactions on Medical Imaging, vol. 18, No. 8, Aug. 1999, pp. 686-699.
Yang, J., et al., "Novel Approach for 3-D Reconstruction of Coronary Arteries from Two Uncalibrated Angiographic Images", IEEE Transactions on Image Processing, vol. 18, No. 7, Jul. 2009, pp. 1563-1572.
Zhang, W., et al., "3D Vessel Tree Reconstruction from Rotational C-arm Projections by Multi-view Stereo Reconstruction", APCMBE 2008: 7th Asian-Pacific Conference on Medical and Biological Engineering, IFMBE Proceedings, vol. 19, Jan. 2008, pp. 434-441, ISBN: 1680-0737.
Giovanni Jacopo Ughi, et al., "Clinical Characterization of Coronary Atherosclerosis With Dual-Modality OCT and Near-Infrared Autofluorescence Imaging", JACC: Cardiovascular Imaging, Nov. 2016 (in press), pp. 1-11.
Guillermo J. Tearney, et al., "A Report From the International Working Group for Intravascular Optical Coherence Tomography Standardization and Validation", Consensus Standards for Acquisition, Measurement, and Reporting of Intravascular Optical Coherence Tomography Studies, Journal of the American College of Cardiology, vol. 59, No. 12, Mar. 20, 2012, pp. 1058-1072.
Giovanni Jacopo Ughi, et al., "Automated tissue characterization of in vivo atherosclerotic plaques by intravascular optical coherence tomography images", Biomedical Optics Express, vol. 4, No. 7, Jul. 1, 2013, pp. 1014-1030.
Giovanni Jacopo Ughi, et al., "Clinical Characterization of Coronary Atherosclerosis With Dual-Modality OCT and Near-Infrared Autofluorescence Imaging", JACC: Cardiovascular Imaging, 2016 (In press).
Ernest Horsley, "Imaging for the Future; Intravascular Optical Coherence Tomography", Sep. 10, 2016; https://www.slideshare.net/ErnestHorsley/coronary-optical-coherence-tomography-oct-angio-coregistration-acr-and-metal-stent-optimisation-mso-softwarefrom.
OPTIS™, Stent Optimization Software, St. Jude Medical, Inc., Last updated Feb. 10, 2017; https://www.sjmglobal.com/professionals/resources-and-reimbursement/technical-resources/vascular/intravascular-diagnostics-and-imaging/intravascular-diagnostics-and-imaging-system-ffr-oct/optis-metallic-stent-optimization-software?halert=show&clset=92f57278-460e-4300-b7fe-89e52a04194f%3acadddb93-fcc4-47f2-8ceb-fd88f01ca17f.

* cited by examiner

METHOD FOR DISPLAYING AN ANATOMICAL IMAGE OF A CORONARY ARTERY ON A GRAPHICAL USER INTERFACE

CROSS-REFERENCE TO RELATED APPLICATION(S)

This application relates, and claims priority, to U.S. Provisional Application Ser. No. 62/474,248, filed Mar. 21, 2017, the entire disclosure of which is incorporated by reference herein in its entirety.

BACKGROUND

Field of the Disclosure

The present disclosure relates in general to an anatomical image of a blood vessel enhanced with structural and molecular information, and more particularly, to a method for displaying an anatomical image of a coronary artery with qualitative and quantitative information from an intravascular imaging system overlaid on the anatomical image.

Description of the Related Art

Percutaneous coronary intervention (PCI) has been improved by innovative imaging modalities including coronary angiography and intravascular imaging. Coronary angiography is a medical imaging technique used to visualize lumen of blood vessels and organs of the body. Coronary angiography is also used to guide a catheter insertion to a blood vessel. Coronary angiography provides images that include longitudinal silhouettes of coronary arteries. Coronary angiography image is one type of an anatomical image of blood vessels. Viewing the longitudinal silhouettes of the coronary arteries on a monitor or display helps an interventional cardiologist guide the catheter accordingly. The ability to guide the catheter to a lesion by angiography is why most interventional cardiologists in the United States use only coronary angiography during a PCI procedure.

Another type of imaging modality for PCI includes an intravascular imaging system which provides cross-sectional information of coronary arteries. Intravascular imaging, such as intravascular ultrasound (IVUS) and optical coherence tomography (OCT), provide more precise lesion information. Intravascular imaging may provide more precise information with respect to lumen size, plaque morphology, and implanted devices than a coronary angiography. However, one reason why IVUS and OCT are not commonly used in a PCI procedure is that it is difficult to guide a catheter to a lesion using only IVUS or OCT. Furthermore, when viewing the intravascular image frame of a coronary artery, it may be difficult for an interventional cardiologist to determine what location along the longitudinal silhouette of the coronary artery in an angiography image the IVUS or OCT image was acquired. In other words, the cross-section of the IVUS or OCT image is difficult to locate when viewing an anatomical image of the coronary artery such as an angiography image.

One method for using both an angiography image and an intravascular imaging modality includes displaying an angiography image side-by-side with an intravascular image on a display or monitor. This allows the interventional cardiologist to use the angiography image as a guide for the catheter as well as review the intravascular image frame to obtain more precise lesion information. However, there are issues when displaying an angiography image side-by-side with an intravascular image. One issue when reviewing the intravascular image frame includes the ability to interpret the image efficiently. Another issue for the interventional cardiologist when reviewing an intravascular image side-by-side with an angiography image is the determination of where along the longitudinal portion of the blood vessel in the angiography image is the cross-section occurring from the intravascular imaging.

Thus, there is a need in the art for a method of displaying an anatomical image such as an angiography image that includes information obtained from an intravascular imaging system or systems.

SUMMARY

The present disclosure is directed to a method for displaying an anatomical image to enhance a user's understanding of the anatomical image of a blood vessel to quickly interpret structural and molecular information obtained from an intravascular imaging system. The user is able to interpret the information obtained from an intravascular imaging system without displaying or reviewing intravascular image frames either alone or side-by-side with the anatomical image. The present disclosure is directed to overlaying qualitative and quantitative information obtained from the intravascular imaging system onto the anatomical image of the blood vessel to more efficiently interpret the structural and molecular information as it pertains to a specific portion of the anatomical image.

One embodiment of the present disclosure is directed to a method for displaying an anatomical image of a coronary artery on a graphical user interface. The method may initiate with acquiring an anatomical image or multiple anatomical images of a coronary artery and acquiring a plurality of intravascular image frames of the coronary artery associated with the anatomical image at a plurality of acquisition locations. The method includes detecting qualitative information from the plurality of intravascular image frames and creating one or more indicator(s) from the qualitative information detected. The method may further proceed by determining a spatial relationship between the anatomical image and the plurality of acquisition locations of the plurality of intravascular image frames and generating its linear representation. The method may continue with displaying the anatomical image of the coronary artery with the linear representation overlaid thereon on a display device. The method may conclude by overlaying the one or more indicator(s) representing at least one type of qualitative information on the anatomical image along the linear representation.

In another embodiment of the present disclosure, a method for displaying an anatomical image of a coronary artery on a graphical user interface is executed by an intravascular imaging system. The intravascular imaging system may display anatomical images with information obtained from the intravascular imaging system and overlaid onto a displayed anatomical image to improve a user's understanding of the anatomical image.

In another embodiment of the present disclosure, a method for displaying an anatomical image of a coronary artery is executed by a processor configured to execute various steps such as acquiring anatomical images and intravascular image frames. Such that the anatomical image may be displayed on a display device with information obtained from an intravascular imaging system and overlaid onto the displayed anatomical image to improve a user's understanding of the anatomical image.

Another embodiment of the present disclosure relates to a non-transitory computer-readable medium encoded with a plurality of processor-executable instructions to perform a method for displaying an anatomical image of a coronary artery with information obtained from an intravascular imaging system and overlaid onto the displayed anatomical image.

Further features of the present disclosure will become apparent from the following description of exemplary embodiments with reference to the attached drawings.

DETAILED DESCRIPTION

The following description is of certain illustrative embodiments, although other embodiments may include alternatives, equivalents, and modifications. Additionally, the illustrative embodiments may include several novel features, and a particular feature may not be essential to practice the devices, systems, and methods described herein.

The present disclosure includes a feature for displaying an anatomical image to assist a user during review of the anatomical image of a blood vessel to quickly interpret structural and molecular information obtained from an intravascular imaging system. The user may interpret or review the information obtained from an intravascular imaging system without having to review an intravascular image frame. The present disclosure is directed to overlaying qualitative and quantitative information obtained from the intravascular imaging system onto the anatomical image of the blood vessel in a manner in which a user may more efficiently interpret the structural and molecular information as it pertains to a specific portion of the anatomical image.

Figure 1:
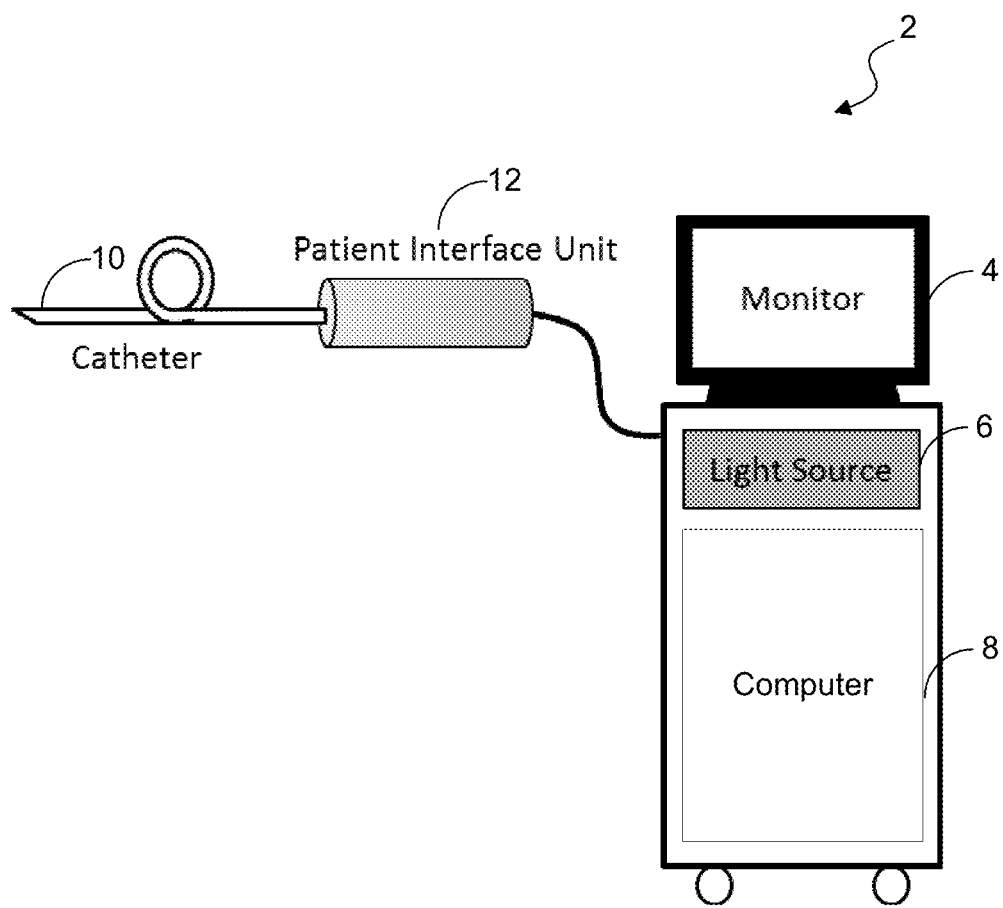
FIG. 1 is a diagram showing a multimodal intravascular imaging system that can execute various steps to display an anatomical image of a coronary artery in accordance with one or more aspects of the present disclosure.

FIG. 1 shows an exemplary multimodality optical coherence tomography (MM-OCT) system 02 for acquiring intravascular image frames in accordance with the present disclosure. The MM-OCT system 02 includes a monitor 04 for displaying an anatomical image of a blood vessel. Information acquired from the intravascular image frames of the MM-OCT system 02 may be overlaid onto the anatomical image of the blood vessel and displayed. Although an MM-OCT system 02 is shown in FIG. 1, the type of intravascular imaging system that may be used in accordance with the present disclosure is not limited to an MM-OCT system. Other intravascular imaging systems that may be used include an optical coherence tomography (OCT) system or an intravascular ultrasound (IVUS) system by way of example.

The anatomical image to be displayed may be acquired from a variety of different anatomical imaging systems. The anatomical imaging system may include an angiography system that produces angiography image frames, computed tomography (CT), CT angiography, magnetic resonance imaging (MRI) or cardiac MRI by way of example. The term anatomical image is used interchangeably with angiography image throughout the present disclosure unless described otherwise. The term blood vessel may also be used interchangeably with coronary artery for purposes of discussion throughout the present disclosure.

Referring back to FIG. 1, the MM-OCT system 02 also includes two light sources 06, a computer 08, a catheter 10, and a patient interface unit 12. The MM-OCT system 02 may acquire intravascular image frames with two different modalities simultaneously. One light source from the two light sources 06 may be used for OCT imaging and the other light source may be used for near infrared (auto-) fluorescence (NIR(A)F) imaging. The NIRF imaging is typically used together with molecularly targeted fluorescent contrast agents that may provide enhanced contrast. Both NIRAF and NIRF imaging may reveal specific molecular events associated with disease formation and progression in a blood vessel and more particularly in a coronary artery.

The catheter 10 functions as a light irradiator and a data collection probe that is disposed in the lumen of a particular blood vessel, such as for example, a coronary artery. The catheter 10 typically includes a probe tip, one or more radiopaque markers, an optical fiber, and a torque wire. The probe tip may include one or more data collection systems. The catheter 10 is threaded in a patient's artery to obtain images of the coronary artery. A patient interface unit 12 includes a motor which can be controlled by a processor associated with the computer 08. The processor may perform all the steps for image processing and controls the information to be displayed on the monitor 04. The motor of the patient interface unit 12 can be used to pull back the torque wire. This pullback procedure obtains images of the blood vessel. The pullback path may represent a co-registration path, and is also known as a region of interest (ROI) path.

A processor associated with the computer 08 may be programmed to process, one or more intravascular image frame datasets of a blood vessel. The processor may also be configured to process an anatomical image of the blood vessel such as an angiography image for example. The anatomical image may be stored in an imaging database associated with the computer 08.

Figure 2:
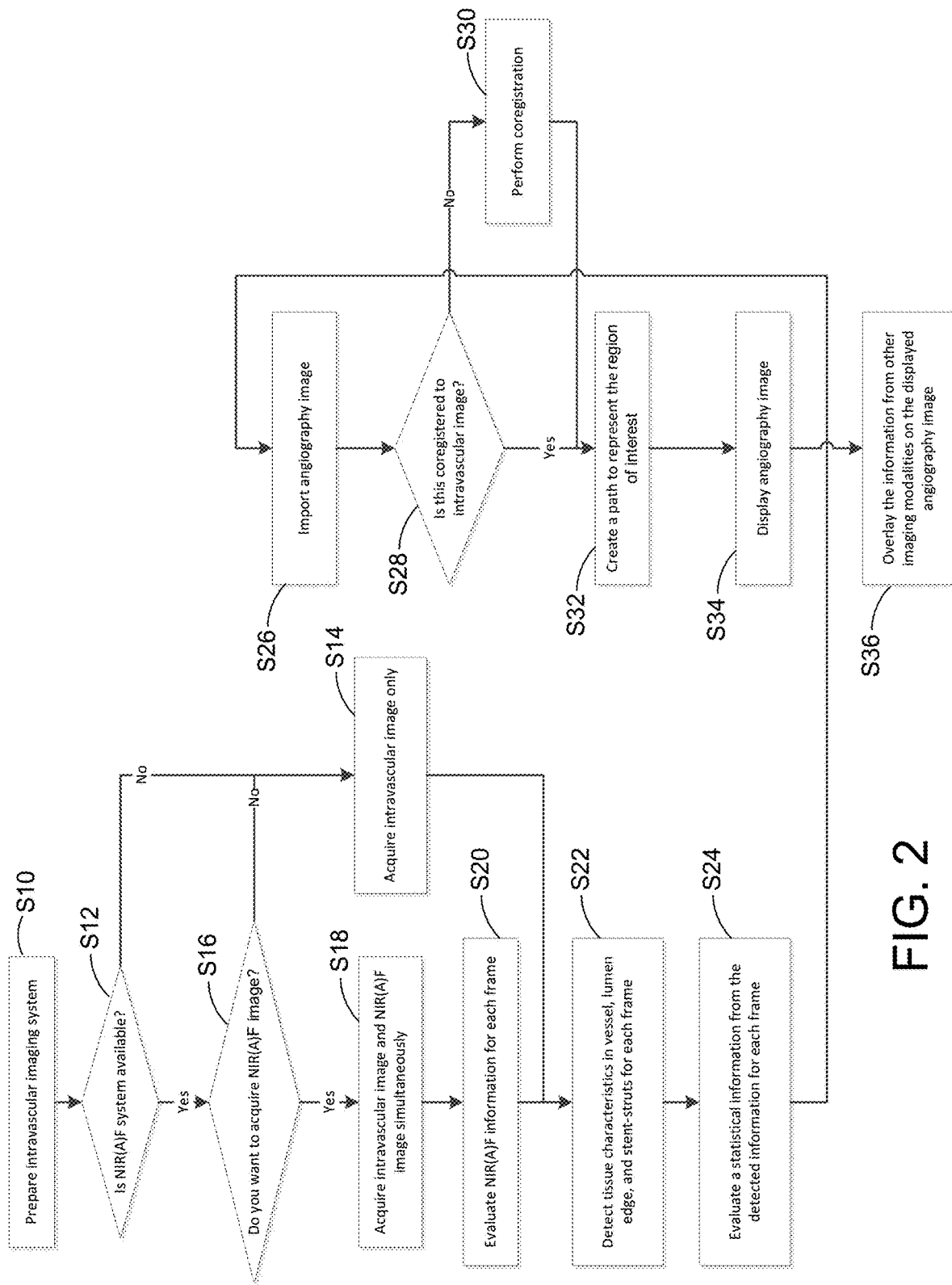
FIG. 2 is a flowchart illustrating various image processing steps in accordance with one or more aspects of the present disclosure.

The present disclosure focuses on how to display information obtained and interpreted from an intravascular imaging modality such as the MM-OCT system 02 described above in a manner that users can better understand and use more efficiently in a clinical setting. An overall exemplary image processing workflow is illustrated in FIG. 2. The process is initiated with preparing the intravascular imaging system (MM-OCT system 02 of FIG. 1) in step S10. In step S12, it is determined whether or not the NIR(A)F system is available. If the NIR(A)F system is not available (no in step S12), the intravascular imaging system acquires intravascular image frames in step S14 without acquiring NIR(A)F image frames. Alternatively, if the NIR(A)F system is available (yes in step S12), a user of the intravascular imaging system decides whether to acquire the NIR(A)F image frames in step S16. If the user decides not to acquire the NIR(A)F image frames (no in step S16), the intravascular image frames are acquired in step S14. If the user decides to acquire the NIR(A)F image frames (yes in step S16), both the intravascular image frames and NIR(A)F image frames are acquired simultaneously in step S18.

In step S20, the NIR(A)F information is evaluated by a processor for each of the acquired image frames. Subsequently, tissue characteristics in a blood vessel, a lumen edge and stent-struts for each image frame are detected using the processor in step S22. The detected information includes qualitative information that refers to information that is directly obtained from intravascular imaging such as IVUS, OCT, or MM-OCT. The qualitative information may also include plaque morphology, thrombus, stent thrombus, stent apposition, stent malapposition, stent edge dissection, tissue protrusion, stent-strut coverage, neointima formation and NIR(A)F by way of example.

In step S24, the processor proceeds to calculate statistical information from the detected information for each intravascular image frame acquired. The statistical information is quantitative information that refers to the information that is calculated from the qualitative information. Some examples of quantitative information may include plaque size, lumen area and diameter, stent area and diameter, stent malapposition distance, stent malapposition severity, stent underexpansion severity, resorption rate of a bio-absorbable stent, NIR(A)F intensity and area and physiological measurement (e.g., fractional flow reserve) by way of example.

In step S26, the processor imports an angiography image representative of the anatomical image. Although step S26 indicates that the angiography image may be imported after image processing of the intravascular image frames, these steps are interchangeable and may also be processed in parallel. For example, the processor may import the angiography image(s) prior to acquiring the intravascular image frames and/or the NIR(A)F image frames. Alternatively, the angiography image(s) may be imported by the processor when the intravascular image frames are acquired by the MM-OCT system 02. In step S28, it is determined whether the imported angiography image of the blood vessel is co-registered with the acquired intravascular image frames. If the processor determines that the angiography image is not co-registered with the intravascular image frames (no in step S28), co-registration is performed in step S30. Each acquired intravascular image frame has an acquisition location that may be visually represented on the angiography image.

Still referring to FIG. 2, if it is determined in step S28 that the angiography image and the intravascular image frames are co-registered, a co-registration path is created. The co-registration path may represent the ROI path generated in step S32. Typically the ROI path is the area where IVUS/OCT pullback is performed. The generation of the ROI path is determined by the processor. The generation of the ROI path can be done for entire angiography frame or for multiple selected angiography frames. Subsequently in step S34, the angiography image including the ROI path is displayed. In step S36 the qualitative information obtained from the intravascular imaging system and/or the NIR(A)F system is overlaid on the displayed angiography image. The quantitative information calculated from the qualitative information may be overlaid on the displayed angiography image as well in step S36.

Figure 3A:
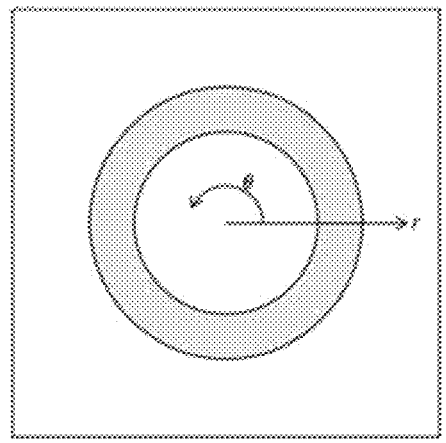
FIG. 3A is a diagram illustrating a cross-sectional image of a lumen of a blood vessel.
Figure 3B:
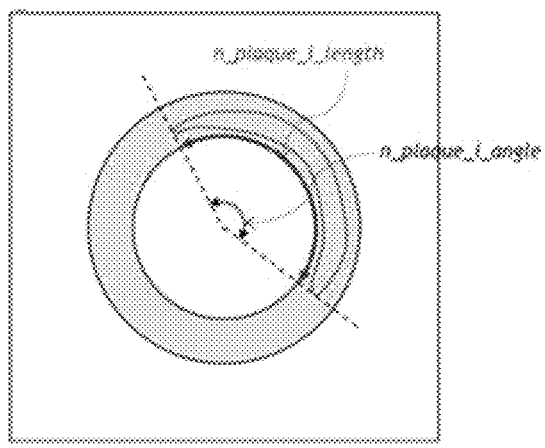
FIG. 3B is a diagram illustrating plaque length and plaque angle with respect to a cross-section image of a lumen of a blood vessel.

To obtain the qualitative information and/or the quantitative information as shown in Table 1 below, the following image processing steps proceed. First, an intravascular image frame (n-th frame) is selected. In this frame, the lumen, the stent-strut(s), the plaque(s), and the NIR(A)F signal are detected. This detection is performed in the radial direction (r-direction) for each angle θ as shown in FIG. 3A. If any types of plaque are detected, the qualitative information is saved accordingly (n_plaque_i=1, where i represents each plaque type), and the length along the lumen edge and the angle where the plaque is distributed are calculated and saved as part of the quantitative information (n_plaque_i_length, n_plaque_i_angle) as shown in FIG. 3B.

If a NIR(A)F signal is detected and if the signals intensity is higher than a threshold amount, the qualitative information is saved as n_NIR(A)F=1, and the maximum/minimum/averaged NIR(A)F intensity and the angle where the higher-than-threshold intensity is detected in θ-direction are saved as the quantitative information (n_NIR(A)F_max, n_NIR(A)F_min, n_NIR(A)F_ave, n_NIR(A)F_angle). The threshold can be determined by a user or can be pre-determined as a default based on clinical evidence.

The lumen area n_lumen is calculated as the inner area of the detected lumen edge. If multiple stent-struts are detected, the stent area n_stent is calculated by interpolating the stent-strut(s) as an oval. In addition, the diameters of the lumen and/or the stent are calculated and its maximum and minimum values are saved as well (n_lumen_φmax, n_lumen_φmin, n_stent_φmax, n_stent_φmin). If a user adjusts the location of the lumen edge and/or the stent-strut(s) from the detected location, the information of the area and the diameters are updated accordingly.

When n_stent is calculated, the stent underexpansion is calculated and saved as n_stent_expan. One example method to calculate n_stent_expan is the ratio of n_stent to the lumen area of the frame that is used to determine the size of a balloon catheter and/or a stent before PCI. The severity n_stent_expan_serverity is categorized either 1 (severe), 2 (moderate), or 3 (mild) by comparing n_stent_expan to the threshold for each level that is determined by a user or based on clinical evidence. Alternatively, the severity n_stent_expan_serverity may be categorized as either 1 (yes) or 0 (no).

When the stent-strut(s) is detected, the distance between the stent-strut and the lumen is calculated in the r-direction for each detected stent-strut, and the maximum/minimum/averaged distance is saved as the quantitative information (n_stent_malap_max, n_stent_malap_min, n_stent_malap_ave). The severity information (n_stent_malap_severity) is saved as 1 (severe), 2 (moderate), or 3 (mild) by comparing the calculated distance to the severity threshold for each level that can be pre-set based on the clinical evidence and can be modified by a user. Alternatively, the severity n_stent_expan_serverity may be categorized as either 1 (yes) or 0 (no). The calculated distance is selected from n_stent_malap_max, n_stent_malap_min, or n_stent_malap_ave, and this selection is based on a user's preference or clinical evidence.

The information of the stent edge dissection is saved as n_stent_dissec=1 (yes) or 0 (no).

When the bio-absorbable stent is implanted, its resorption rate can be quantified. If the bio-absorbable stent-strut is visualized as a closed region, the area of the detected closed region is calculated for each detected stent-strut. The ratio of the calculated area to its original area is evaluated for each detected stent-strut, and the maximum/minimum/averaged values are saved as n_stent_bio_max, n_stent_bio_min, and n_stent_bio_ave. The original area needs to be input by a user based on the manufacturer's information.

Table 1 shows all the qualitative and quantitative information that has been described and is used in this description by way of example and not limited to any other types of qualitative and quantitative information.

TABLE 1

Qualitative and Quantitative Information

| Detection | Qualitative Information | Quantitative Information |
|---|---|---|
| Plaque | n_plaque_i | n_plaque_i_length, n_plaque_i_angle |
| NIR(A)F | n_NIR(A)F | n_NIR(A)F_max, n_NIR(A)F_min, n_NIR(A)F_ave, n_NIR(A)F_angle |
| Lumen Stent-strut | n_stent_expan_serverity n_stent_malap_severity n_stent_dissec | n_lumen, n_lumen_φmax, n_lumen_φmin n_stent, n_stent_φmax, n_stent_φmin n_stent_expan n_stent_malap_max, n_stent_malap_min, n_stent_malap_ave n_stent_bio_max, n_stent_bio_min, and n_stent_bio_ave |

Referring back to FIG. 2, in step S28 it is determined whether or not the angiography image is co-registered with the acquired intravascular image frames. Co-registration is done in the following process. A catheter with a radiopaque marker at the tip is used for intravascular imaging. The processor finds the radiopaque marker on the angiography image frames by searching a darkest point/mark in the image frames. The co-registration location is determined by finding a point that is proximal to the detected marker location with the known distance between the marker and the optical lens for imaging along the longitudinal direction of the coronary artery. There are other ways of co-registration, and the present disclosure is not limited to this one particular example of co-registration method.

Figure 4:
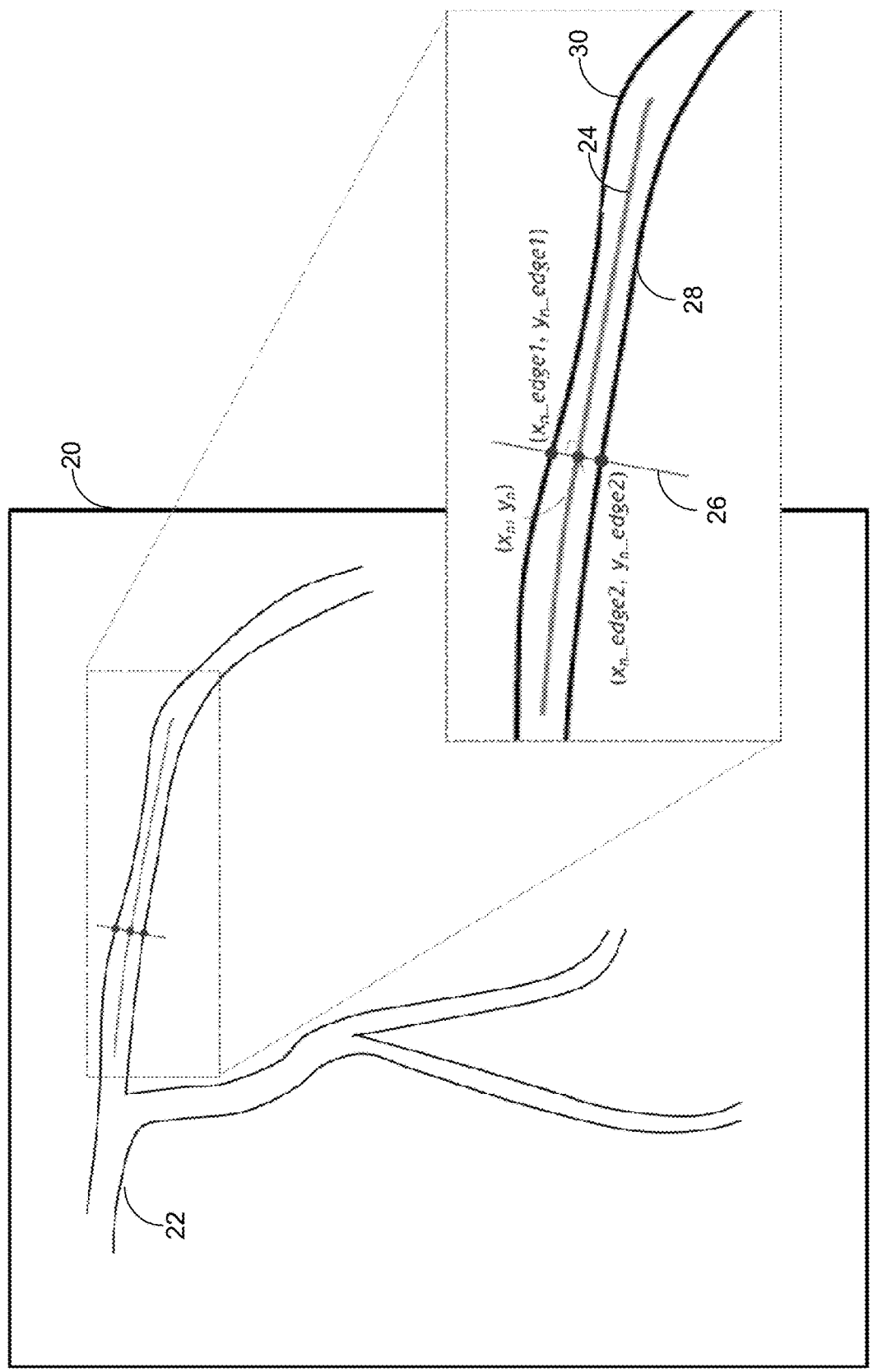
FIG. 4 is a diagram illustrating an angiography image in accordance with one or more aspects of the present disclosure.

FIG. 4 is a diagram of an angiography image 20 acquired from an angiography system. The angiography image 20 is representative of what a user may view on a display or graphical user interface. A coronary artery 22 is shown in the angiography image 20. Although a coronary artery 22 is shown in FIG. 4, the present disclosure is applicable to any artery and/or blood vessel to be displayed on a display device such as a monitor. An angiography image may be obtained in a catheterization laboratory by injecting a patient with a radio-opaque contrast agent into the blood vessel and imaging using X-ray based techniques such as fluoroscopy by way of example and not of limitation. The coronary artery 22 shown in FIG. 4 includes a first lumen edge 28 and a second lumen edge 30. The area between the first lumen edge 28 and the second lumen edge 30 represents the interior of the coronary artery in the angiography image 20. The angiography image 20 is used to measure a lumen diameter, as well as visualize the vessel curvature, and most importantly to guide any catheter based devices, such as balloon catheter with or without stent and intravascular imaging catheter.

The zoomed in portion of the coronary artery in FIG. 4 is for explanation purposes and reveals three coordinates, a cross-sectional line 26 of a portion of the artery as well as the ROI path 24 that may be used for determining the overlaying location of information obtained from intravascular imaging onto the angiography image 20. Prior to determining the overlaying location, the angiography image 20 must be co-registered with an intravascular image frame during image processing described in FIG. 2.

The angiography image 20 here has a zoomed in portion for purposes of explanation to view the coordinates that are used to determine an overlaying location for the intravascular imaging information obtained by an intravascular imaging system. First, the location $(x_n, y_n)$ where the selected intravascular image frame, n-th frame, is acquired is found in the displayed angiography frame 20 using the co-registration information. Then, the intersection of the lumen edge (28, 30) and the line 26 (n_line) that goes through the co-registration location and that is perpendicular to the ROI path 24 is detected in the displayed angiography frame 20 [$(x_n\_edge1, y_n\_edge1)$ and $(x_n\_edge2, y_n\_edge2)$]. The information is overlaid on n_line within $(x_n\_edge1, y_n\_edge1)$ and $(x_n\_edge2, y_n\_edge2)$. The coordinate of the overlaid location is $(x_n\_info\_j, y_n\_info\_j)$, where j represents each qualitative information, such as n_plaque_i, n_NIR(A)F, n_stent_expan_serverity, n_stent_malap_severity, and n_stent_dissec.

For each j, the distance between $(x_n, y_n)$ and $(x_n\_info\_j, y_n\_info\_j)$ and the direction of $(x_n\_info\_j, y_n\_info\_j)$ on n_line relative to $(x_n, y_n)$ must be the same. To enable displaying multiple types of information, the distance between $(x_n, y_n)$ and $(x_n\_info\_j, y_n\_info\_j)$ must be different in a pixelated coordinate system for different j with a certain value. If the information is overlaid within the inner area of the lumen, it should not be overlaid on $(x_n\_edge1, y_n\_edge1)$ or $(x_n\_edge2, y_n\_edge2)$. If $(x_{n-1}\_info\_j, y_{n-1}\_info\_j)$ and $(x_n\_info\_j, y_n\_info\_j)$ are not located next to each other in the pixelated display, the shortest path between these two points are created and the information that is overlaid either on $(x_{n-1}\_info\_j, y_{n-1}\_info\_j)$ or $(x_n\_info\_j, y_n\_info\_j)$ is overlaid. The information to be overlaid on the newly created path is selected based on the pixelated distance between the point on the path and $(x_{n-1}\_info\_i, y_{n-1}\_info\_j)$ or $(x_n\_info\_i, y_n\_info\_j)$—the information on the closer distance is chosen. The same process is applied if $(x_n\_info\_j, y_n\_info\_j)$ and $(x_{n+1}\_info\_j, y_{n+1}\_info\_j)$ are not next to each other in the pixelated display.

In another embodiment of the present disclosure if a user prefers to overlay the qualitative information as a single line on the displayed angiography image, the user is first asked to select the qualitative information to overlay: for pre-PCI stage, the selection is either n_plaque_i or n_NIR(A)F; for post-PCI stage, the selection is either n_plaque_i, n_NIR(A)F, n_stent_expan_serverity, or n_stent_malap_severity, and being able to add n_stent_dissec if a user prefers. If a user selects n_plaque_i and if i is plural (i.e., the multiple types of plaque are detected in the entire intravascular imaging frames), the user can select to overlay either one plaque type or multiple plaque types. If a user selects one plaque type, the user needs to specify the type to overlay. If a user selects multiple types, the user specifies the types to overlay and the processor creates a new value based on n_plaque_i_length and n_plaque_i_angle. The created new value can be overlaid as a gradation path using multiple colors.

The default overlaid location is $(x_n, y_n)$ for the selected n-th frame. Based on a user's preference, the overlaid location can be changed within $(x_n\_edge1, y_n\_edge1)$ and $(x_n\_edge2, y_n\_edge2)$ on n_line, or on the lumen edge, i.e., $(x_n\_edge1, y_n\_edge1)$ or $(x_n\_edge2, y_n\_edge2)$. The same restriction and the interpolation steps are applied between the adjacent intravascular image frames.

Figure 5:
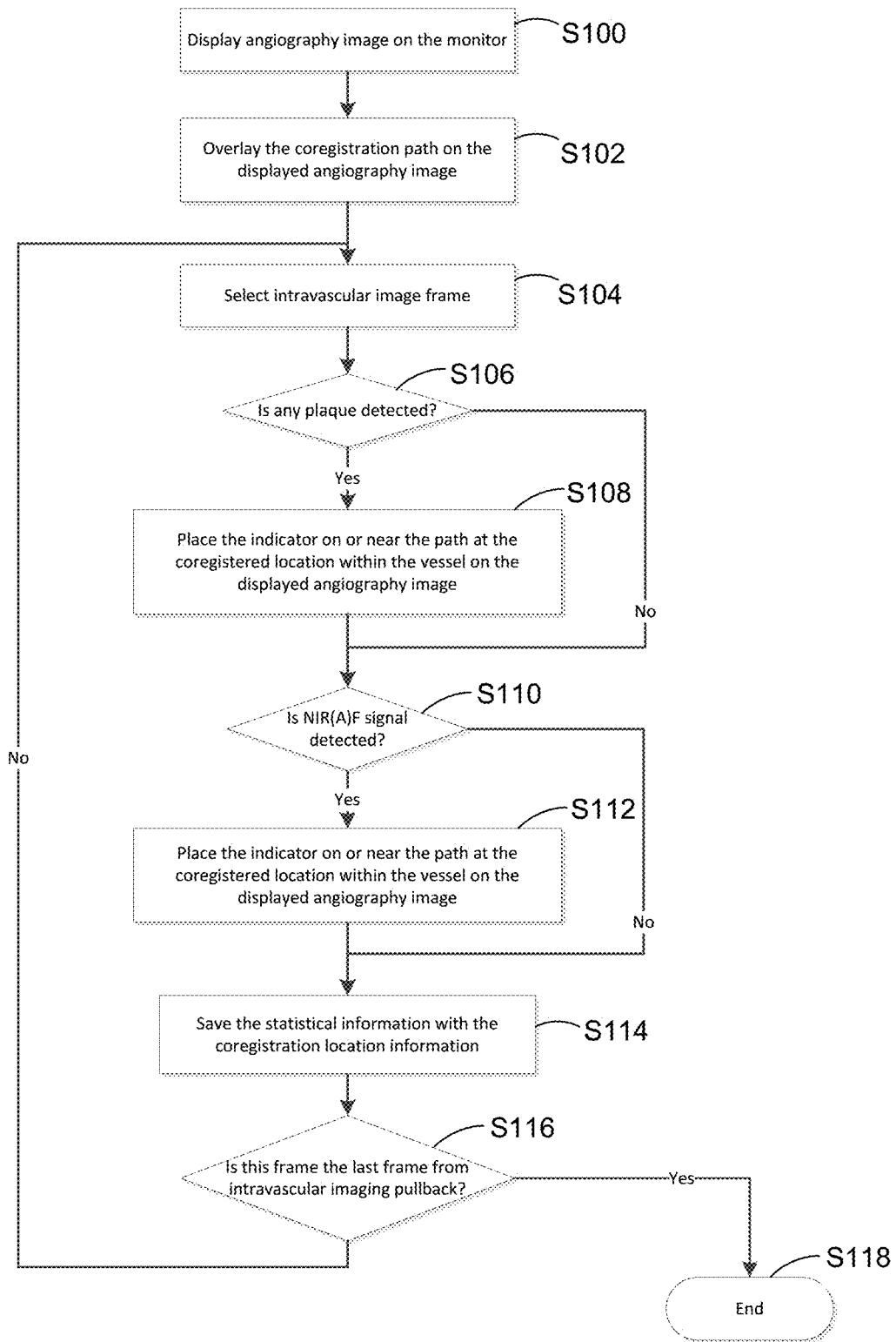
FIG. 5 is a flowchart illustrating various image processing steps prior to percutaneous coronary intervention in accordance with one or more aspects of the present disclosure.

FIG. 5 is a flowchart illustrating multiple steps for overlaying information from intravascular image frames onto an angiography image prior to PCI. In step S100, a selected angiography image is displayed on a monitor. In step S102, the co-registration path or ROI path is generated and overlaid on the displayed angiography image. The overlaid location is determined by co-registration. FIG. 5 does not contain the lumen detection or its statistical calculation, but these processes may be performed simultaneously with the steps of detection and calculation for other features.

In step S104, an intravascular image frame is selected. After selection of the intravascular image frame, it is determined whether or not any plaque is detected based on the intravascular image frame in step S106. If plaque is detected (Yes in step S106), an indicator on or near the ROI path at the co-registered location within the coronary artery is displayed on the angiography image.

If no plaque is detected in step S106, step S108 is skipped and in step S110 it is determined whether a NIR(A)F signal is detected. If it is determined in step S110 that a NIR(A)F signal is detected, the process proceeds to step S112. In step S112 an indicator on or near the ROI path at the co-registered location within the coronary artery is displayed on the angiography image.

If no NIR(A)F signal is detected in step S110, then step S112 is skipped and the statistical information associated with the co-registration location information is saved in step S114. In step S116 it is determined whether the selected intravascular image frame is the last frame from intravascular imaging pullback. If the selected intravascular frame is not the last frame (No in step S116), the process repeats starting at step S104 and another intravascular image frame is selected. This loop occurs until the selected intravascular image frame is the last frame from intravascular imaging pullback. If the intravascular image frame is the last frame from imaging pullback (Yes in step S116), the process for overlaying the information from the intravascular image frames onto the angiography image is completed and ends at step S118. The information may be overlaid within the interior area representing the coronary artery without blocking other anatomical features.

In another embodiment of the present disclosure, when the lumen of the coronary artery 22 is detected in the selected intravascular frame in step S104, the system can check the quality of the selected intravascular image frame based on a user preference. If it is determined that the selected intravascular image frame is not of sufficient image quality when (1) the lumen cannot be detected in a certain angle range, (2) the averaged gray-scale levels are within a small difference between the area in the detected lumen and the area in the vessel, or (3) the detected lumen border is not connected in the pixelated display. If the system judges the selected intravascular frame is low quality and if a user would like to, the system will not detect any other features or calculate the quantitative information.

If a certain number of continuous intravascular image frames are judged as low-quality frames, a user can select whether the ROI path 24 at the corresponding location is overlaid or not on the displayed angiography image. If a user selects to overlay the ROI path 24, a text box to display the quantitative information or a cursor to select the location to display the quantitative information will not appear on the displayed angiography image at the corresponding location, even though a user selects to display the quantitative information. If the number of the continuous intravascular image frames with low quality is less than a threshold, the qualitative information can be overlaid based on the qualitative information from an adjacent intravascular image frame. The quantitative information corresponding to the selected low-quality intravascular frame will not be shown. The threshold for the number of the continuous frames can be determined based on a user's preference or clinical evidence.

Figure 6:
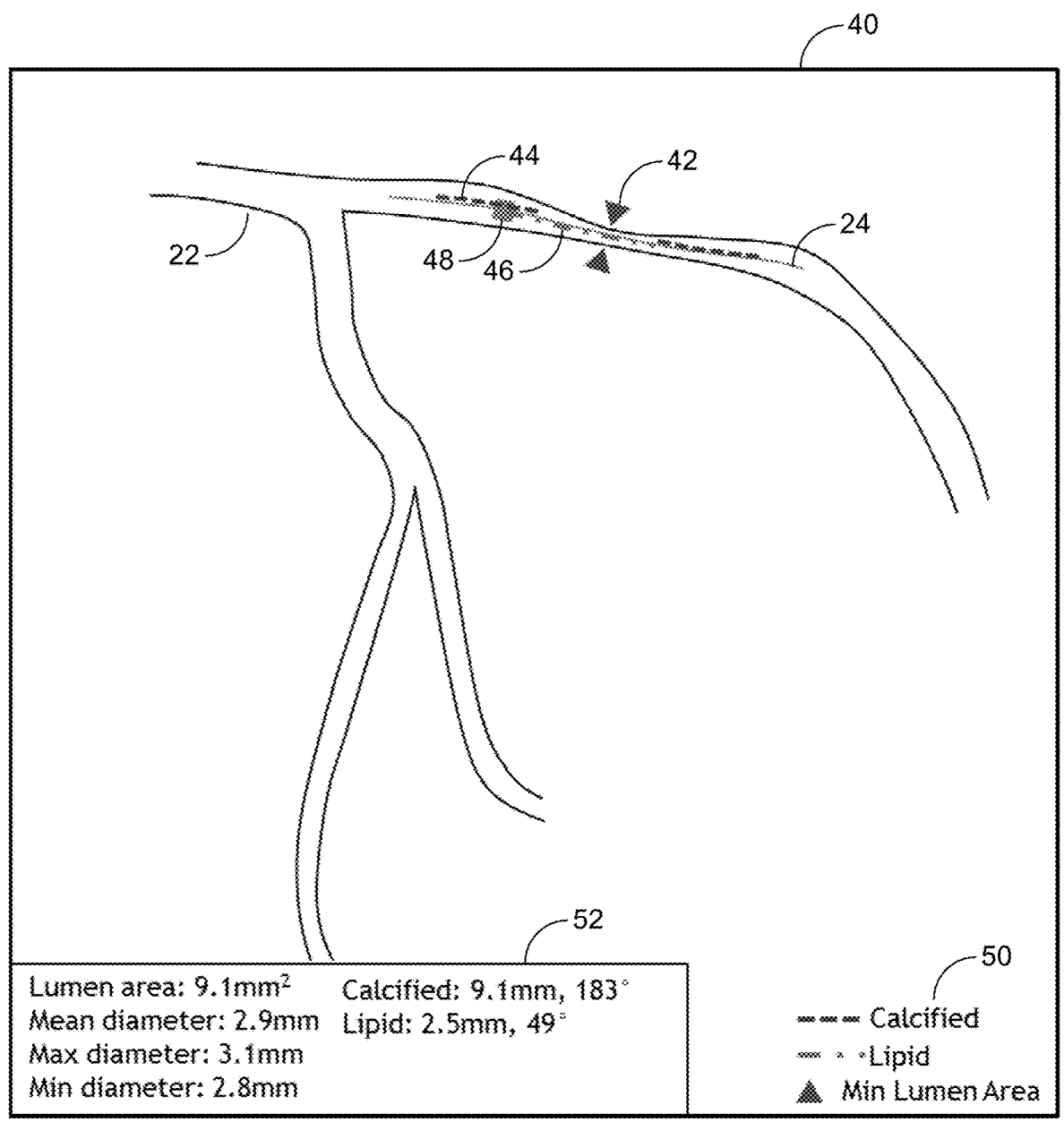
FIG. 6 is a diagram illustrating a graphical user interface in accordance with one or more aspects of the present disclosure.

FIG. 6 illustrates an exemplary graphical user interface (GUI) 40 that may be displayed on the monitor 04 of the MM-OCT system 02. The GUI 40 of FIG. 6 contains one view that displays an angiography image with overlaid qualitative information of the coronary artery from intravascular imaging. The quantitative information is displayed in a text box 52 at the bottom left hand corner of the GUI 40 as text. It is important to note that the text box 52 is located in an area where no anatomical features of the coronary artery 22 are blocked. The GUI 40 includes a cursor 48 that is overlaid on the ROI path 24. A user of the GUI 40 may drag the cursor 48 using a mouse or other input device along the ROI path 24 to obtain updated quantitative information shown in text box 52. The GUI 40 displays updated quantitative information that is collected at the cursor 48 location. The ROI path 24 is overlaid within the coronary artery 22 in a longitudinal direction of the centerline of the coronary artery 22.

Also shown in FIG. 6 are indicators 42 for the location of the minimum lumen area that may be displayed at the edge of the coronary artery 22. A user visually reviewing the GUI 40 may quickly determine the minimum lumen area 42 based on where the indicators 42 are located. The number and the configuration of the indicator(s) are determined based on the location of the other anatomical features near the minimum lumen area, so that the indicator does not block any other anatomical features, such as nearby side branches of the coronary artery 22. The different indices may be displayed at the corner of the GUI 40 in a legend 50.

The qualitative information may be displayed using color and/or different line types (solid, dotted, dashed, etc.) on the monitor. The indicators may be colored and/or specific type of line as shown in FIG. 6. A broken line 44 is used as an indicator for calcified plaque. The indicator 44 for calcified plaque is overlaid in a linear representation on an interior portion of the coronary artery 22. Another broken line 46 in a lighter shade than the broken line 44 is used as an indicator for lipid-rich plaque. The indicator for the lipid-rich plaque is overlaid in a linear representation on the interior portion of the coronary artery 22. The indicators (44, 46) as well as the ROI path 24 are linearly represented within the interior of the coronary artery 22 as well as overlaid such that they are on multiple longitudinal paths at different locations with respect to the radial direction of the coronary artery 22. Although different shades and geometrical shapes are used to distinguish the different indicators in FIG. 6, other methods may be used to distinguish between different indicators such as color coding, etc. FIG. 6 shows the GUI 40 when NIR(A)F information is unavailable.

For pre-PCI, the qualitative information can be overlaid within an inner space of the coronary artery 22, either on or near the ROI path 24 at the co-registration location. The qualitative information overlaid within the inner space of the coronary artery 22 may be overlaid on multiple different longitudinal pathways as shown in FIG. 6. This is so a user reviewing the coronary artery 22 can clearly see the different types of qualitative information overlaid between the lumen edges (28, 30). If the coronary artery 22 is too small, the qualitative information can be displayed at the lumen edge.

A user such as an interventional cardiologist can review the displayed angiography image and using the cursor 48 on the GUI 40 to review updated quantitative information based on an intravascular image frame without having to review the intravascular image frame. The interventional cardiologist can determine whether a percutaneous coronary intervention is required by analyzing the displayed angiography image along with the qualitative and quantitative information overlaid on the angiography image.

Figure 7:
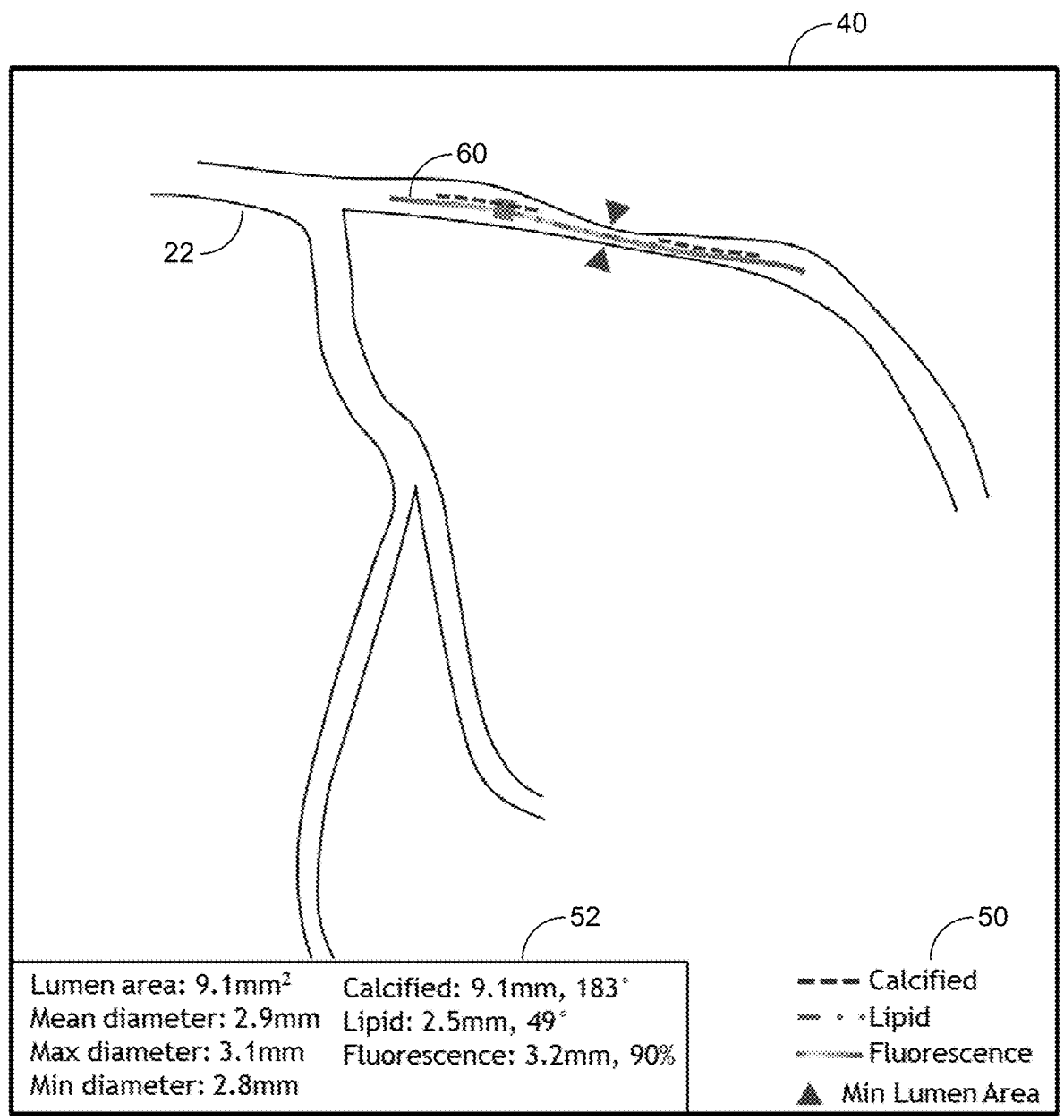
FIG. 7 is a diagram illustrating a graphical user interface including near-infrared autofluorescence in accordance with one or more aspects of the present disclosure.

FIG. 7 illustrates the GUI 40 displaying the angiography image of the coronary artery 22 when NIR(A)F information is available. The GUI 40 of FIG. 7 is similar to FIG. 6 except that FIG. 7 includes both qualitative and quantitative information obtained from NIR(A)F and overlaid on the angiography image as shown. Similarly, it is not necessary for the user to review the actual NIR(A)F image, the user may view the qualitative information as shown overlaid with the coronary artery 22 along the ROI path 24. The quantitative information based on the fluorescence information is calculated and displayed as text based on where the cursor 48 is along the ROI path 24.

In this case, the qualitative NIR(A)F information is displayed as a gradation 60 of the ROI path 24. The gradation 60 is linearly represented along the interior area of the coronary artery 22. When the gradation 60 is used, the overlaid information can be n_NIR(A)F_max, n_NIR(A)F_ave, or a new value that is created based on n_NIR(A)F_max, n_NIR(A)F_min, n_NIR(A)F_ave, and n_NIR(A)F_angle, or any combination from these. When the information is overlaid, any overlaid information should not block any anatomical features that are originated within the ROI path 24 and/or that are located near the ROI path 24. For pre-PCI, the qualitative information can be overlaid within an inner space of vessel, either on or near the ROI path at the co-registration location. If the vessel is too small, the qualitative information can be displayed at the edge of the vessel. In this case the gradation 60 of the NIR(A)F qualitative information is displayed on the centerline of the coronary artery 22 overlapping with the ROI path 24. The legend 50 located in a corner of the GUI 40 is updated to include the fluorescence indicator associated with the gradation 60. The text box 52 is also updated to include the quantitative information associated with the fluorescence.

A user reviewing the angiography image within the GUI 40 can look at different indicators representing calcified plaque, lipid-rich plaque and minimum lumen area for example, obtained from intravascular imaging such as OCT, by looking near the ROI path 24 of the displayed coronary artery 22. It is not necessary for the user to review the OCT image. Furthermore, the qualitative information based on a different imaging modality such as NIR(A)F may be reviewed by the user simply by reviewing the gradation 60 of the fluorescence overlaid on the centerline of the coronary artery 22. The text box 52 includes all the quantitative information based on the two different intravascular imaging modalities so that the user has all the information based on intravascular imaging on the GUI 40 of the angiography image of the coronary artery 22.

Figure 8:
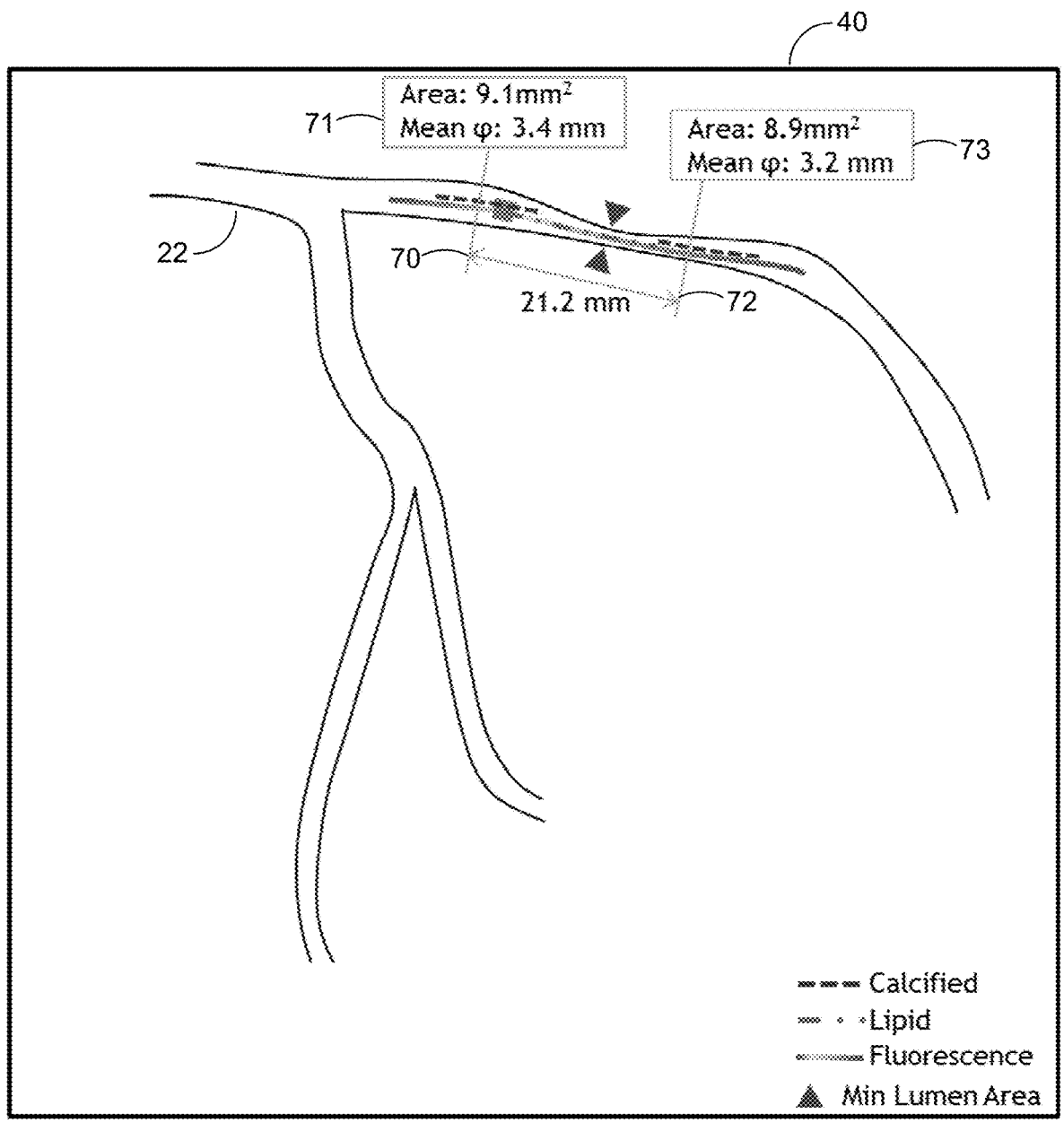
FIG. 8 is a diagram illustrating a graphical user interface at a percutaneous coronary intervention planning stage in accordance with one or more aspects of the present disclosure.
Figure 9:
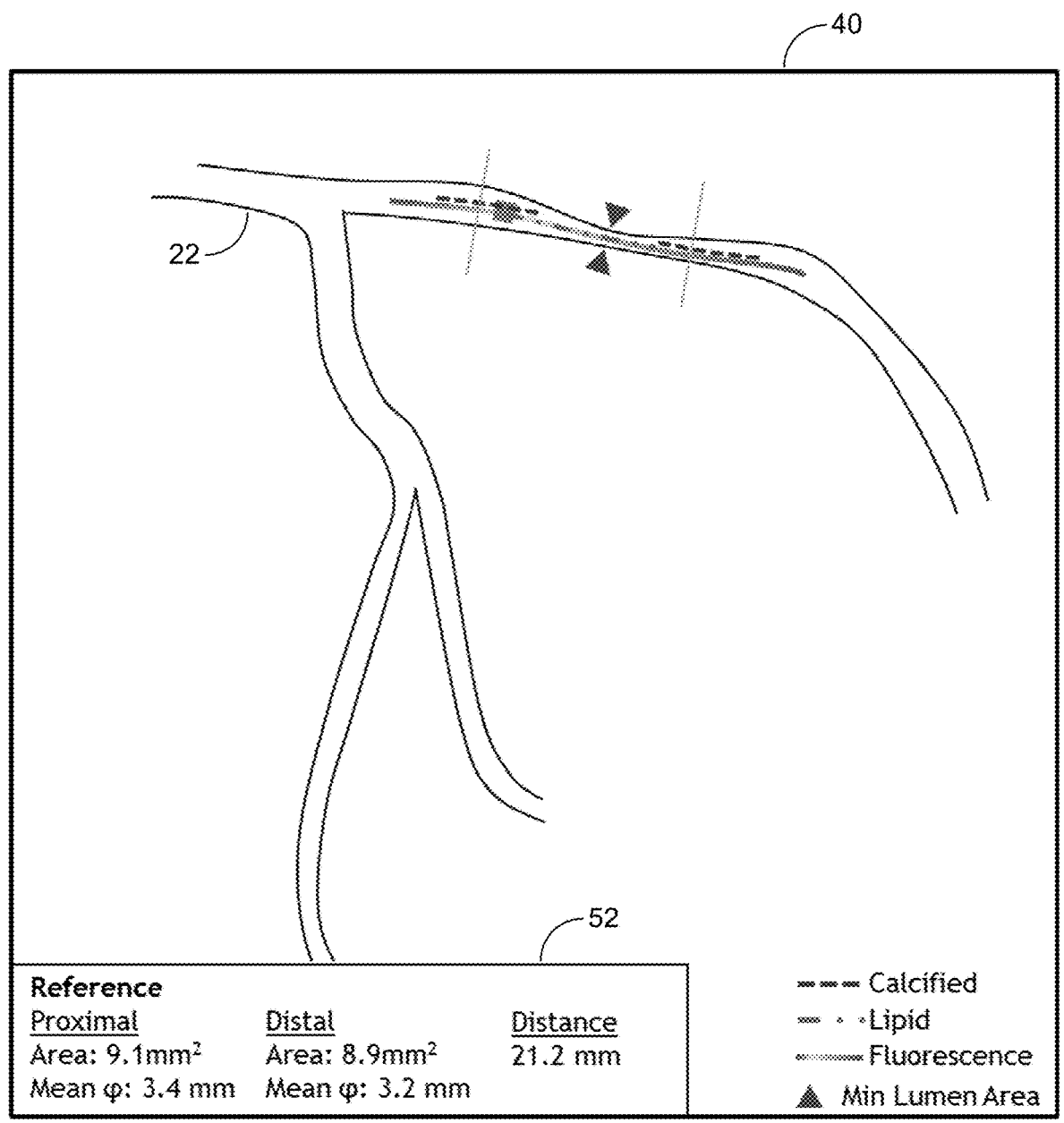
FIG. 9 is a diagram illustrating a graphical user interface at a percutaneous coronary intervention planning stage in accordance with one or more aspects of the present disclosure.

If a user determines after reviewing the GUI 40 that a patient needs PCI, the GUI 40 can be used for the planning stage for PCI. FIG. 8 shows the GUI 40 during the PCI planning stage. A user, such as an interventional cardiologist, can place one or multiple marker(s) (70, 72) on the displayed angiography image of the coronary artery 22 where the user is planning to perform PCI. Once the user places the marker(s) (70, 72), the quantitative information (71, 73), e.g., lumen area and mean lumen diameter, is shown near the marker(s) (70, 72). The user may also select to display the quantitative information at the corner of the displayed angiography image as shown in the text box 52 of FIG. 9. If the user places multiple markers (70, 72), the distance between the markers is automatically calculated and can be displayed in the same manner as the other quantitative information displayed in FIGS. 8 and 9. If the user prefers, the other qualitative information that is overlaid within the inner area of the vessel, such as the information of plaque morphology and/or NIR(A)F, can be removed from the display based on a user preference.

Figure 10:
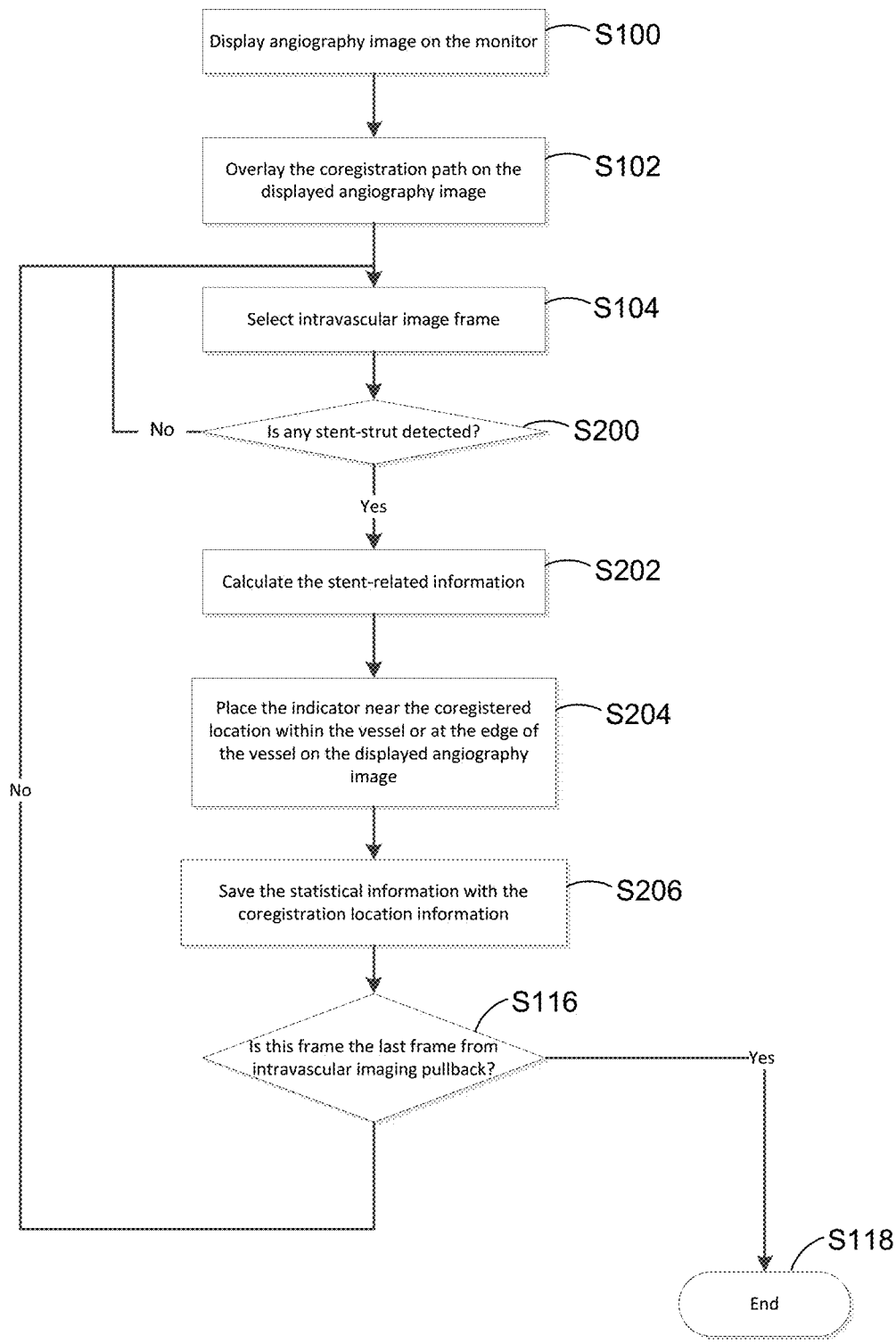
FIG. 10 is a flowchart illustrating various image processing steps at a post-stenting stage in accordance with one or more aspects of the present disclosure.

FIG. 10 is a flowchart illustrating various steps for overlaying information from intravascular imaging onto an anatomical image after PCI to review post-PCI (post-stenting) of the coronary artery on a GUI. FIG. 10 does not contain the lumen detection or the statistical calculation for illustration purposes, but these processes may be performed simultaneously with the steps of detection and calculation for other features. Steps S100, S102 and S104 are the same as the flowchart shown in FIG. 5 which includes displaying the anatomical image on a monitor, overlaying the co-registration path on the displayed anatomical image and selecting an intravascular image frame. Starting at step S200, it is determined whether any stent-strut is detected from the selected intravascular image frame. If no stent-strut is detected in step S200, a different intravascular image frame is selected in step S104. If a stent-strut is detected in step S200 (Yes), stent-related information is calculated in step S202. In step S204, an indicator is placed on or near the co-registration location within the coronary artery or at the lumen edge of the coronary artery on the displayed anatomical image. In step S206, the statistical information associated with the detected stent-strut is saved with the co-registration location information. In step S116 it is determined if the selected intravascular image frame is the last frame from intravascular imaging pullback. If the selected intravascular image frame is the last frame the image processing is ended at step S118. If the selected intravascular image frame is not the last frame from intravascular imaging pullback, the image processing steps are repeated starting at step S104 for selecting a subsequent intravascular image frame.

Figure 11:
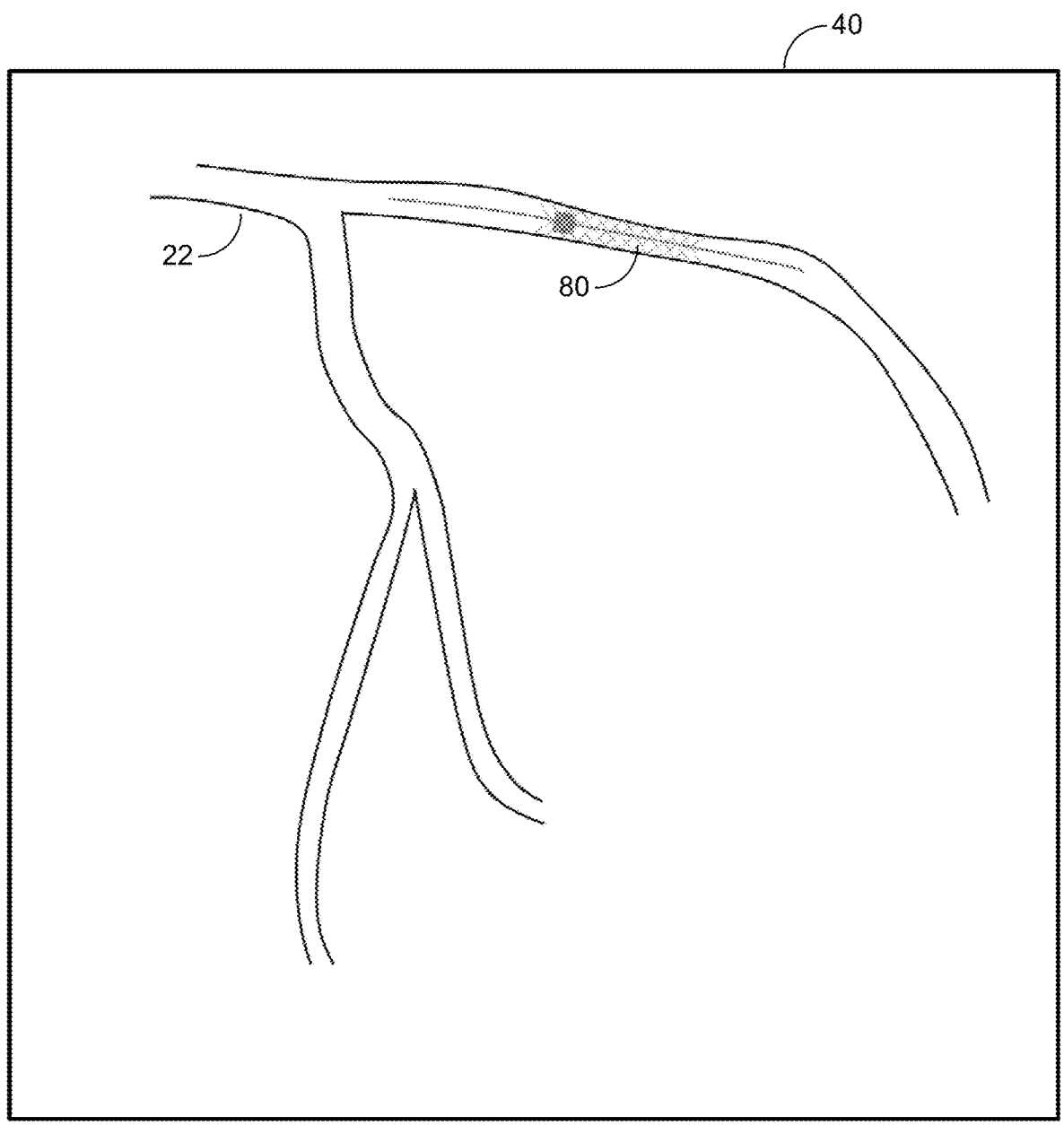
FIG. 11 is a diagram illustrating a graphical user interface for visualizing a stent marker in accordance with one or more aspects of the present disclosure.

FIG. 11 is a diagram of the GUI 40 at a post-PCI (post-stenting) stage. The stent is visualized in FIG. 11. After PCI, the information about the procedural outcomes can be overlaid on the displayed angiography image. If a stent is implanted, an artificial stent marker 80 is overlaid on the displayed angiography image at the location where the stent-strut is detected from the intravascular image frames. The artificial stent marker 80 can mimic the stent structure, as shown in FIG. 11. The user may analyze the GUI 40 and determine exactly where the stent structure is located along the coronary artery 22 without having to review the intravascular image frames in which the location of the stent structure is determined. Further facilitating the user's ability to visualize the stent structure in an angiography image displayed within the GUI 40.

Figure 12:
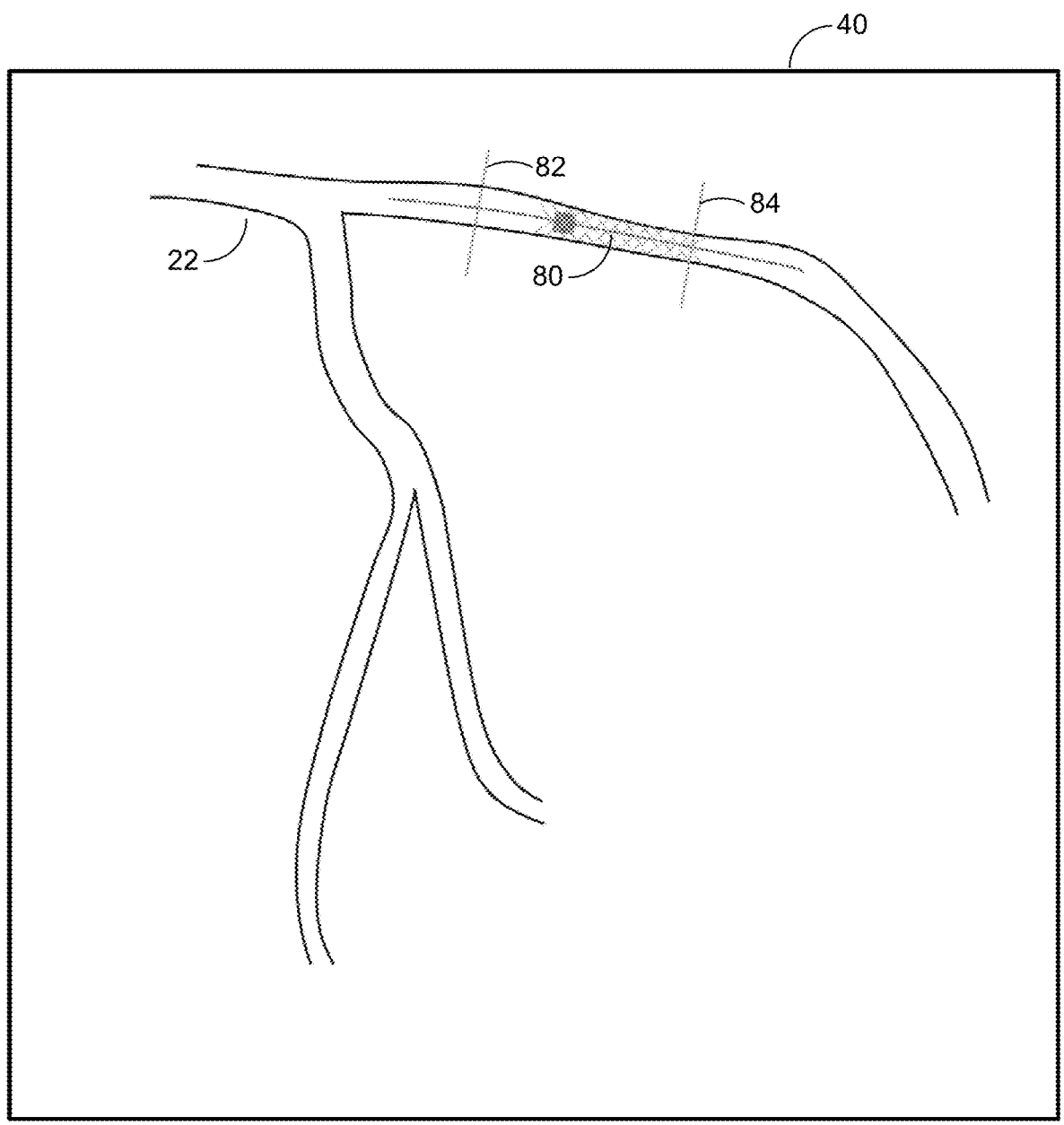
FIG. 12 is a diagram illustrating a graphical user interface for comparing actual and planned stent location in accordance with one or more aspects of the present disclosure.

Referring now to FIG. 12, the GUI 40 is shown at a post-PCI (post-stenting) stage comparing the actual stent location with the planned stent location. If a user wants to compare the planned PCI location and the actual PCI location, the planning marker(s) (82, 84) that is/are specified during PCI planning stage are also overlaid on the coronary artery 22 displayed in the angiography image, as well as the artificial stent marker 80. The planning markers (82, 84) represent the planned stent location. The artificial stent marker 80 represents the actual stent location along the ROI path 24 of the coronary artery 22.

Figure 13:
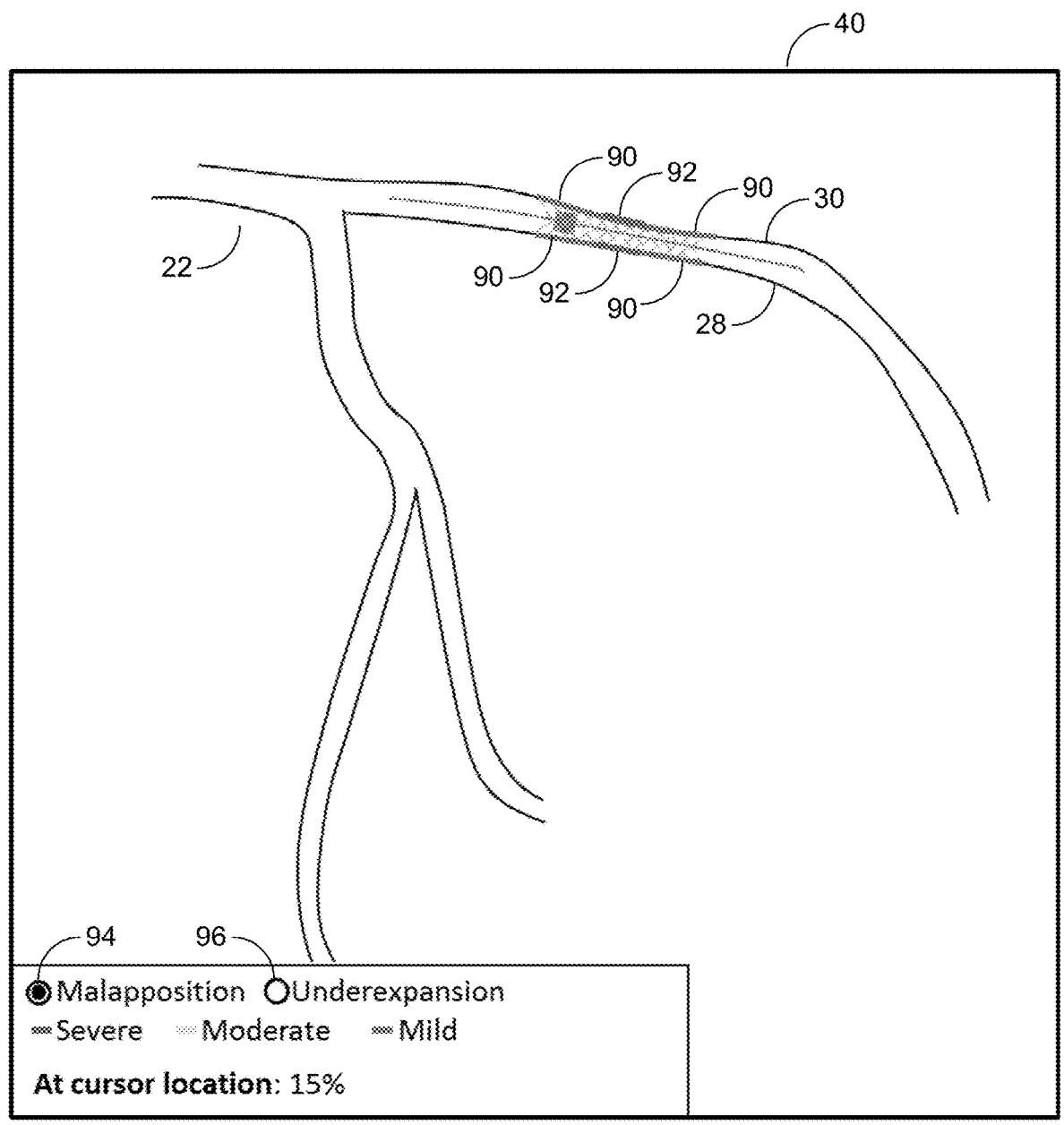
FIG. 13 is a diagram illustrating a graphical user interface for visualizing stent-related information in accordance with one or more aspects of the present disclosure.

FIG. 13 is another schematic diagram of the GUI 40 at post-PCI (post-stenting) stage that allows the user to visualize stent-related information such as stent malapposition or stent underexpansion. For stenting, the qualitative information regarding stent apposition and expansion can be overlaid as a color-coded map or different shades as an indicator on the displayed angiography image. Before overlaying, a user needs to specify which information (stent malapposition or stent underexpansion) should be overlaid. The user may select which information by selecting which information on the GUI 40 via a mouse or keyboard for example.

In FIG. 13, the user has selected stent malapposition as shown by the filled in button 94. If the user would like to review information regarding stent underexpansion the user would select button 96. Then, the information can be overlaid either at the inner space of the coronary artery 22 or at the edge of the lumen along the ROI path 24 at the co-registration location based on a user's preference. If a user wants to know how severe stent malapposition or underexpansion is at a specific location, a cursor may be placed on the ROI path 24 and a user can move it to the desired location. The severity information (a part of the quantitative information) can be shown either near the cursor or at the corner of the GUI 40. In FIG. 13, the severity information is displayed in the corner of the GUI. The severity of the stent malapposition along the lumen edges (28, 30) is reflected in the indicators along the lumen edge. The mild stent malapposition is represented by the indicator 90 along the lumen edges (28, 30) and the severe stent malapposition is represented by the indicator 92.

Figure 14:
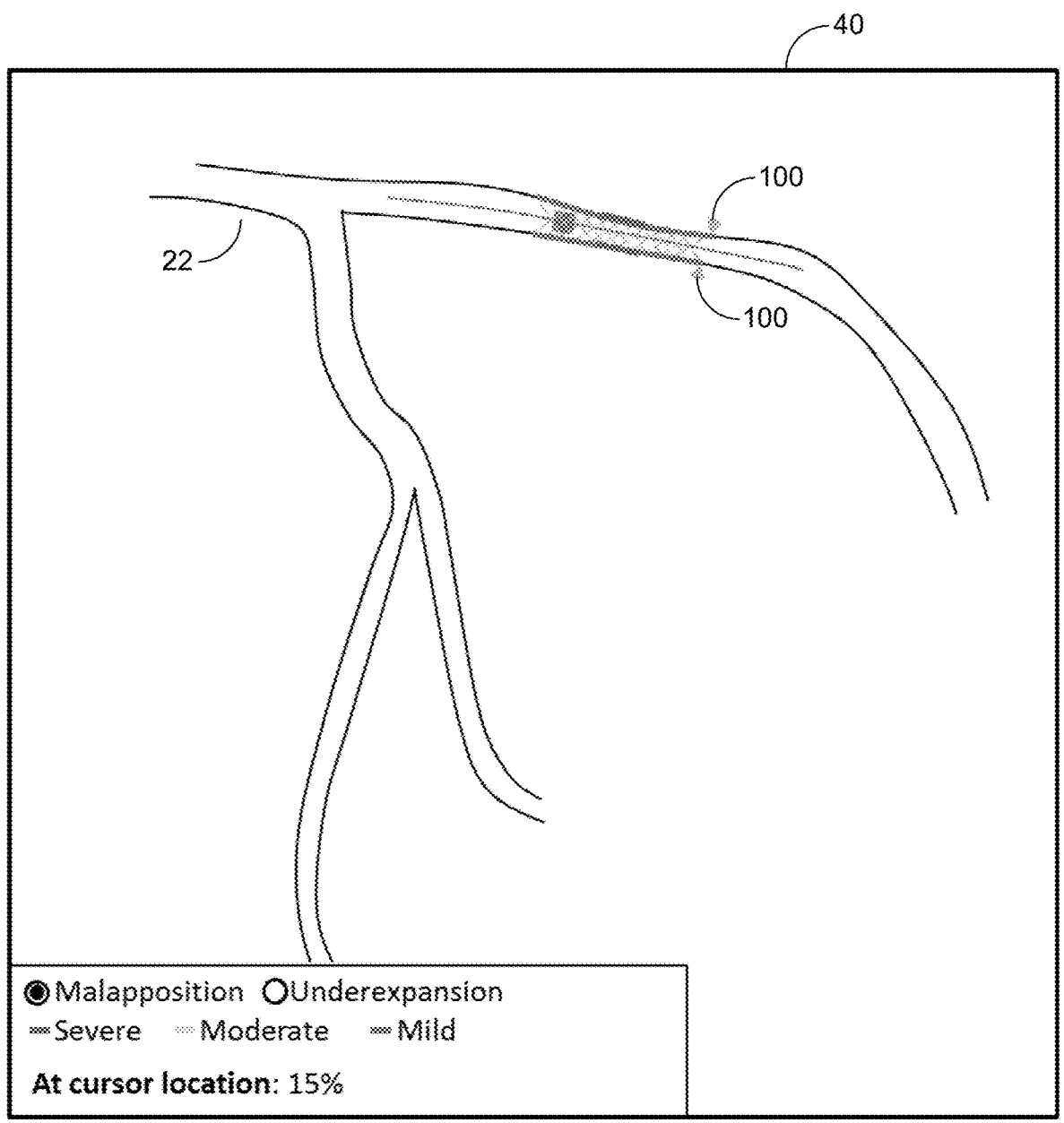
FIG. 14 is a diagram illustrating a graphical user interface for visualizing stent-related information (stent malapposition and stent edge dissection) in accordance with one or more aspects of the present disclosure.

FIG. 14 illustrates the GUI 40 at post-PCI (post-stenting stage) for visualizing stent-related information including stent edge dissection. Moreover, if stent edge dissection is detected in the intravascular imaging, an indicator(s) 100 can be overlaid on the displayed angiography image. The indicator(s) 100 should be shown in a manner by not blocking any other anatomical features nearby. If a user prefers to see other qualitative information, such as n_plaque_i and/or n_NIR(A)F, it can be overlaid on the displayed angiography image in the same manner as the pre-PCI stage.

For post-PCI, the qualitative information that is based on stent-strut detection can be displayed either at the inner space of the vessel or at the edge of the vessel at the co-registration location, while the other qualitative information can be displayed within an inner space of the coronary artery 22. Information related to stent-strut detection can be overlaid at the edge of the coronary artery 22 to enable this specific information to be interpreted more easily when it is displayed near the implanted stent and can be distinguished clearly from the information related to tissue characterization. If a user wants to see the quantitative information, the cursor 48 appears on the ROI path 24 that is overlaid on the displayed angiography image. The user can move the cursor within the longitudinal direction of the ROI path 24. The quantitative information can be displayed as text either near the cursor location or at the corner of the monitor based on the user's preference.

Figure 15:
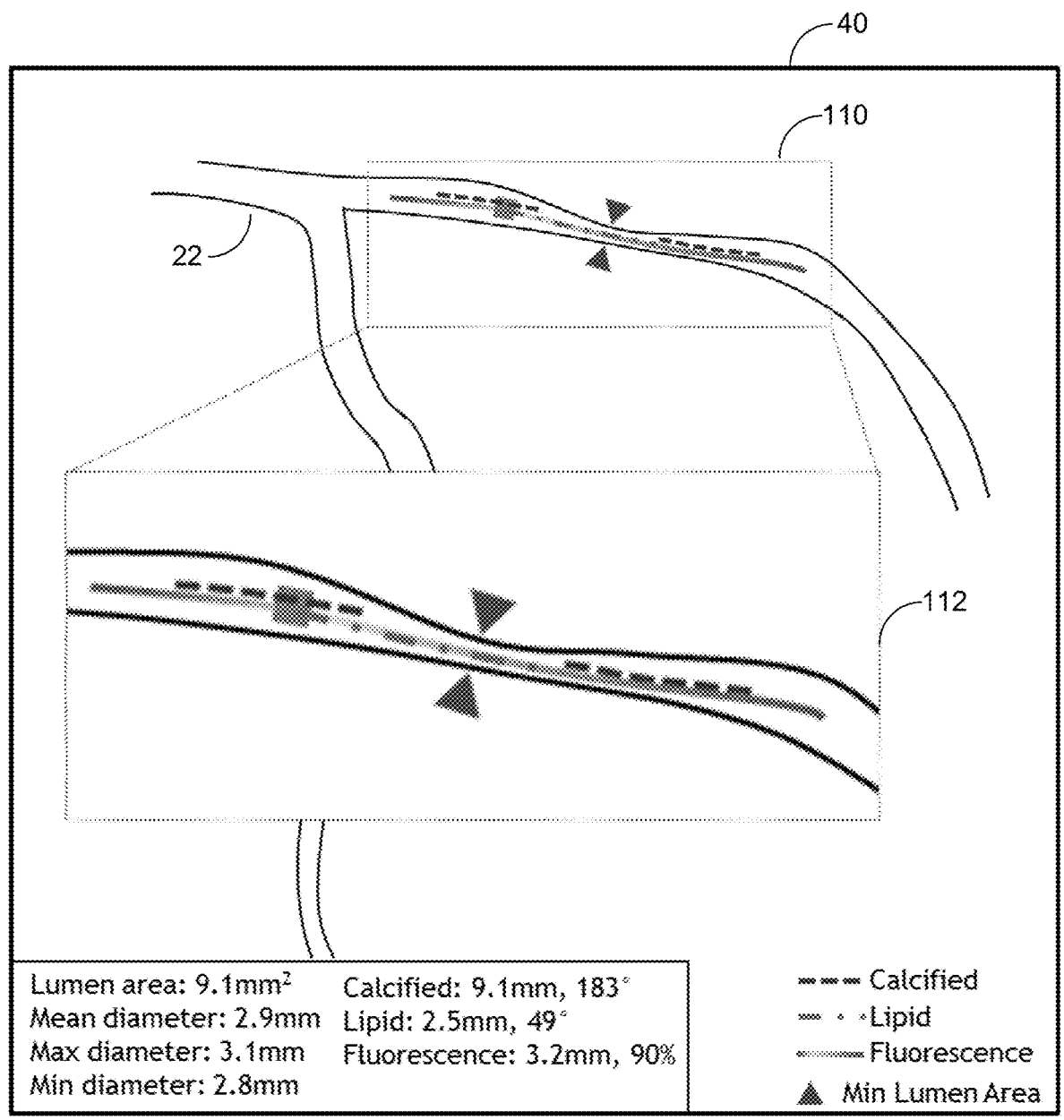
FIG. 15 is a diagram illustrating a graphical user interface with a zoom-in feature of a region of interest path in accordance with one or more aspects of the preset disclosure.

FIG. 15 is a diagram of the GUI 40 similar to the diagram of FIG. 7 but with a zoom-in feature. A region 110 of the coronary artery 22 that includes the ROI path 24 as well as the lumen edges (28, 30) is magnified and displayed within region 112. The zoom-in feature allows the user to zoom-in for an enlarged view of the ROI path 24. In this case, an additional view appears over the original view in the GUI 40. The region 112 does not block the ROI path 24 of the original view including the region 110. The enlarged view in region 112 may provide a user with a better perspective of the qualitative information displayed within the coronary artery 22 of the angiography image shown on the GUI 40. The qualitative information represented by the various indicators in region 112 shows each indicator linearly represented along a longitudinal path of the coronary artery 22.

Figure 16:
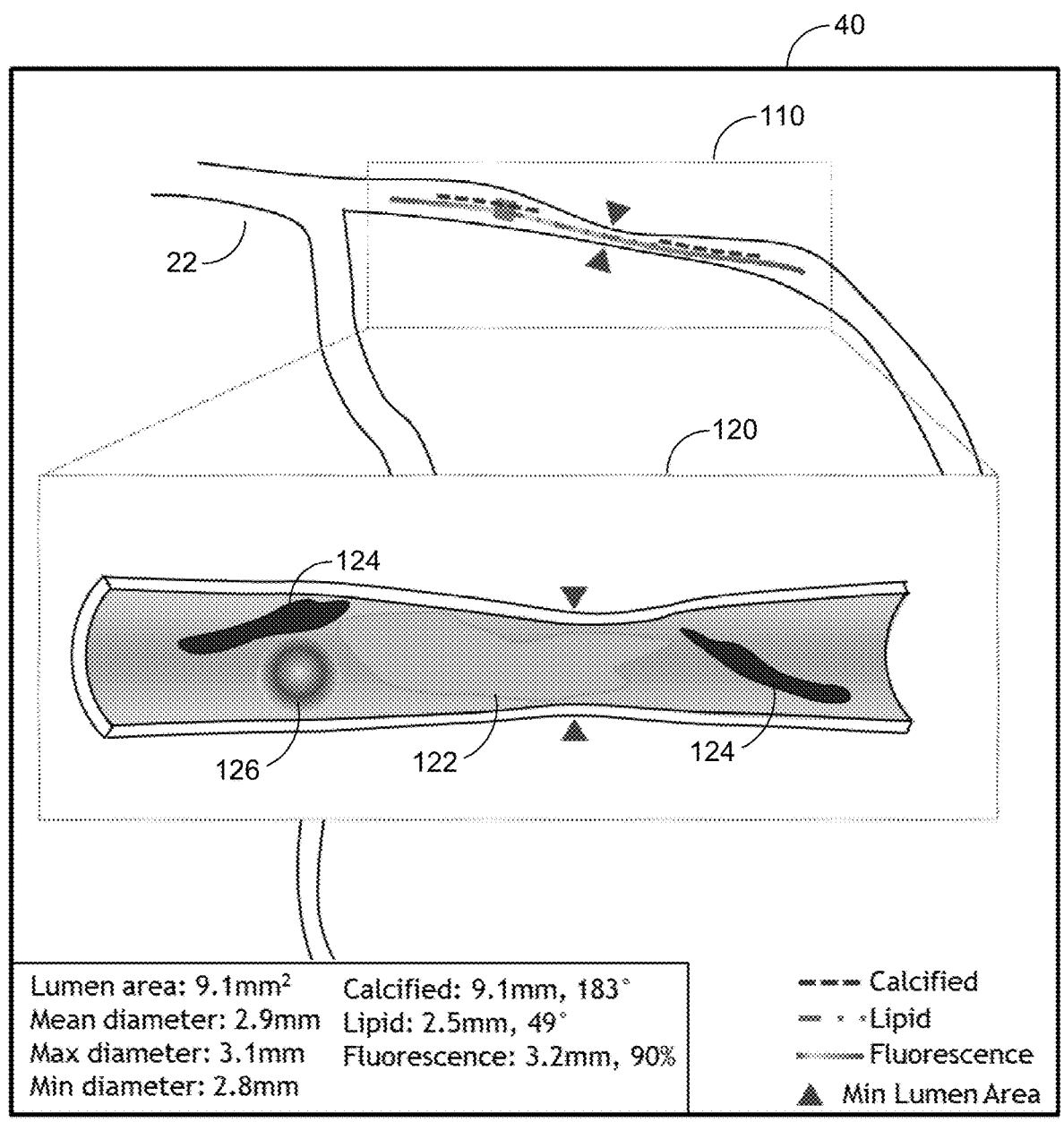
FIG. 16 is a diagram illustrating a graphical user interface with a zoomed-in three-dimensional rendering from intravascular imaging in accordance with one or more aspects of the present disclosure.

The GUI 40 includes various display options the user may view with respect to the region 110 representing the original view of the ROI path 24 of the coronary artery 22. The region 120 allows the user to visualize the qualitative information in a three-dimensional (3D) rendering of the intravascular imaging as shown in FIG. 16. The zoomed-in portion including the 3D rendering allows the user to easily visualize the size and/or area of each plaque as well as visualize the NIR(A)F signal within the angiography image displayed on the GUI 40. The region 120 includes a 3D rendering of the lipid plaque 122, the calcified plaque 124 and NIR(A)F signal intensity 126.

Figure 17:
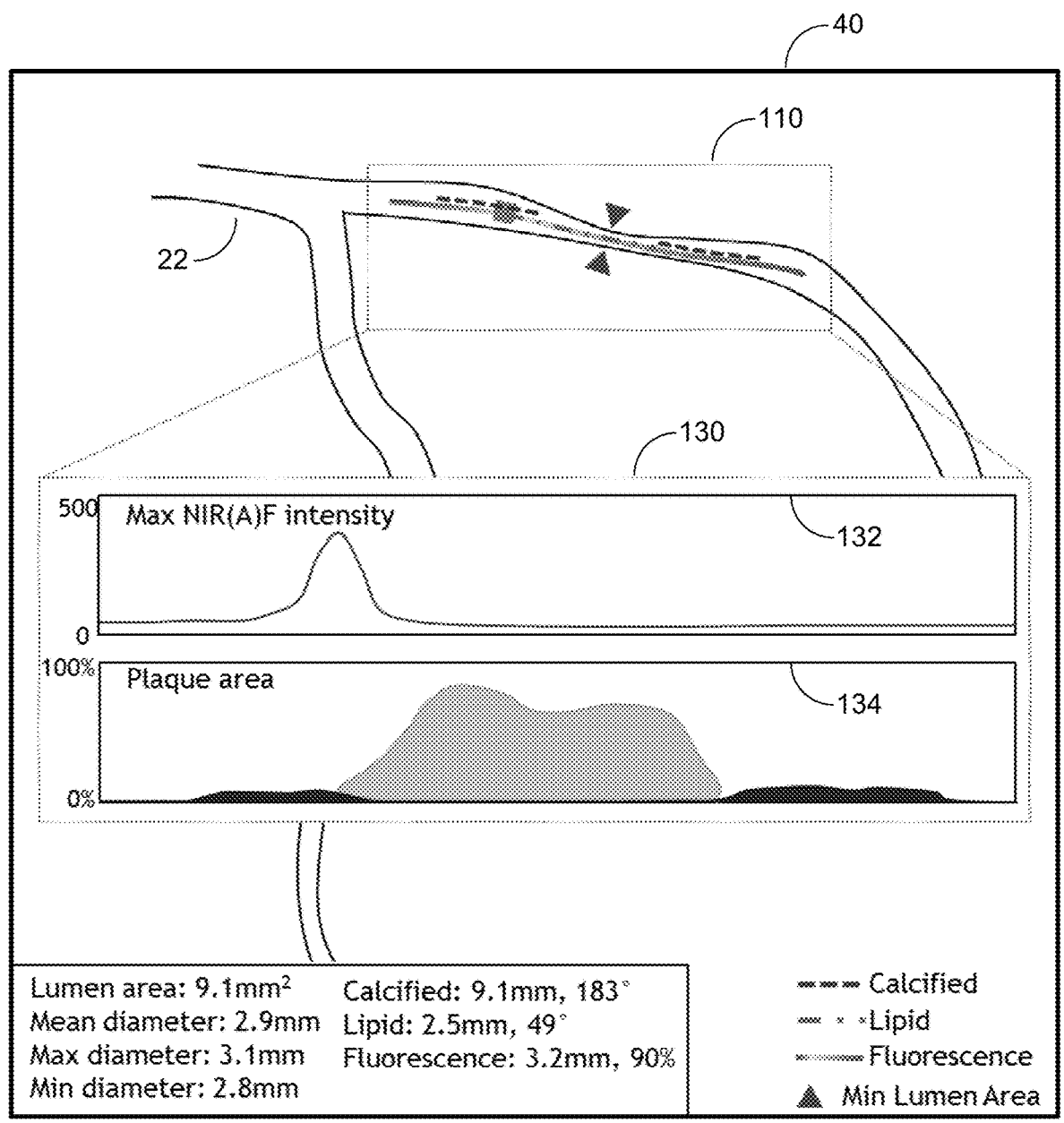
FIG. 17 is a diagram illustrating a graphical user interface with graphs from intravascular imaging in accordance with one or more aspects of the present disclosure.

FIG. 17 shows another display configuration for the GUI 40 that may utilize one or multiple graph(s). The region 130 includes two graphs, one graph 132 represents maximum NIR(A)F intensity. The graph 134 shows the percentage of each plaque type. These examplary GUIs may be used at a pre-PCI stage, the zoom-in feature is also available at PCI planning and post-PCI stages. All the configurations, including the timing to use the zoom-in feature, can be chosen based on a user's preference.

Figure 18:
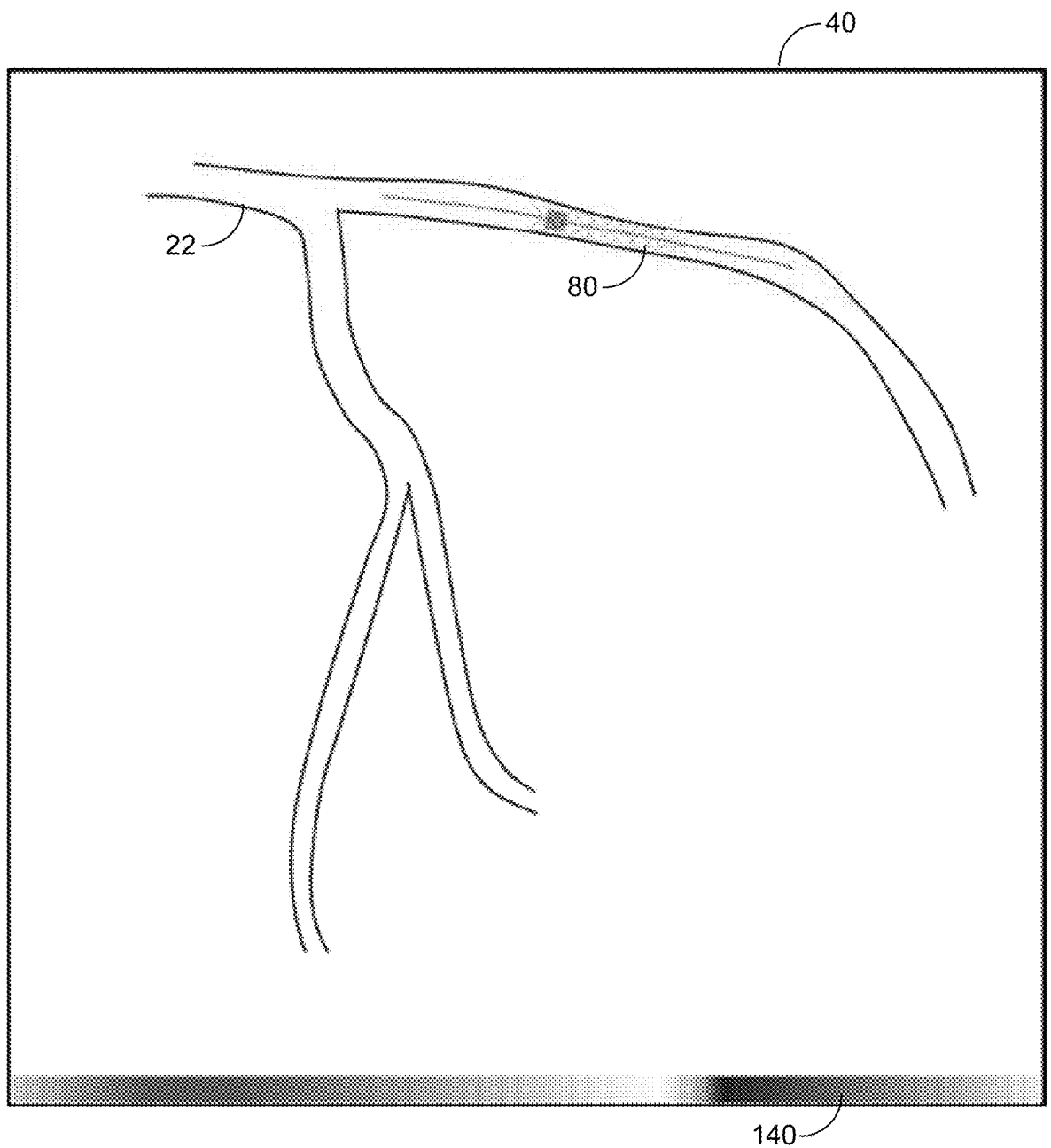
FIG. 18 is a diagram illustrating a graphical user interface with co-registration reliability result in accordance with one or more aspects of the present disclosure.

The GUI has an ability to display a reliability of co-registration if a user wants to view the reliability. If a user chooses to display the reliability, the user can select the method to display and/or may pre-set the default method before the procedure. The reliability may be calculated by a processor while performing co-registration (step S30 in FIG. 2) with an available method. According to one method, the processor estimates the co-registration location for each of the intravascular image frames that are acquired between the two non-consecutive angiography image frames. Subsequently, the estimated co-registration location(s) is compared to the actual co-registration location(s) that is directly detected from the corresponding angiography image frame. The difference between the actual and the estimated locations is considered to be the reliability value. If the reliability value exceeds a certain threshold, an alert may be displayed on the monitor. The threshold can be pre-determined, or can be determined by a user based on a user preference. An alert may include a text message on the display, and/or a graphical output, such as an indicator 140 in FIG. 18, color-coding on the cursor, and an indicator with different line style or different shape. The indicator 140 may be color coded to enable a user to quickly recognize a reliability value.

Figure 19:
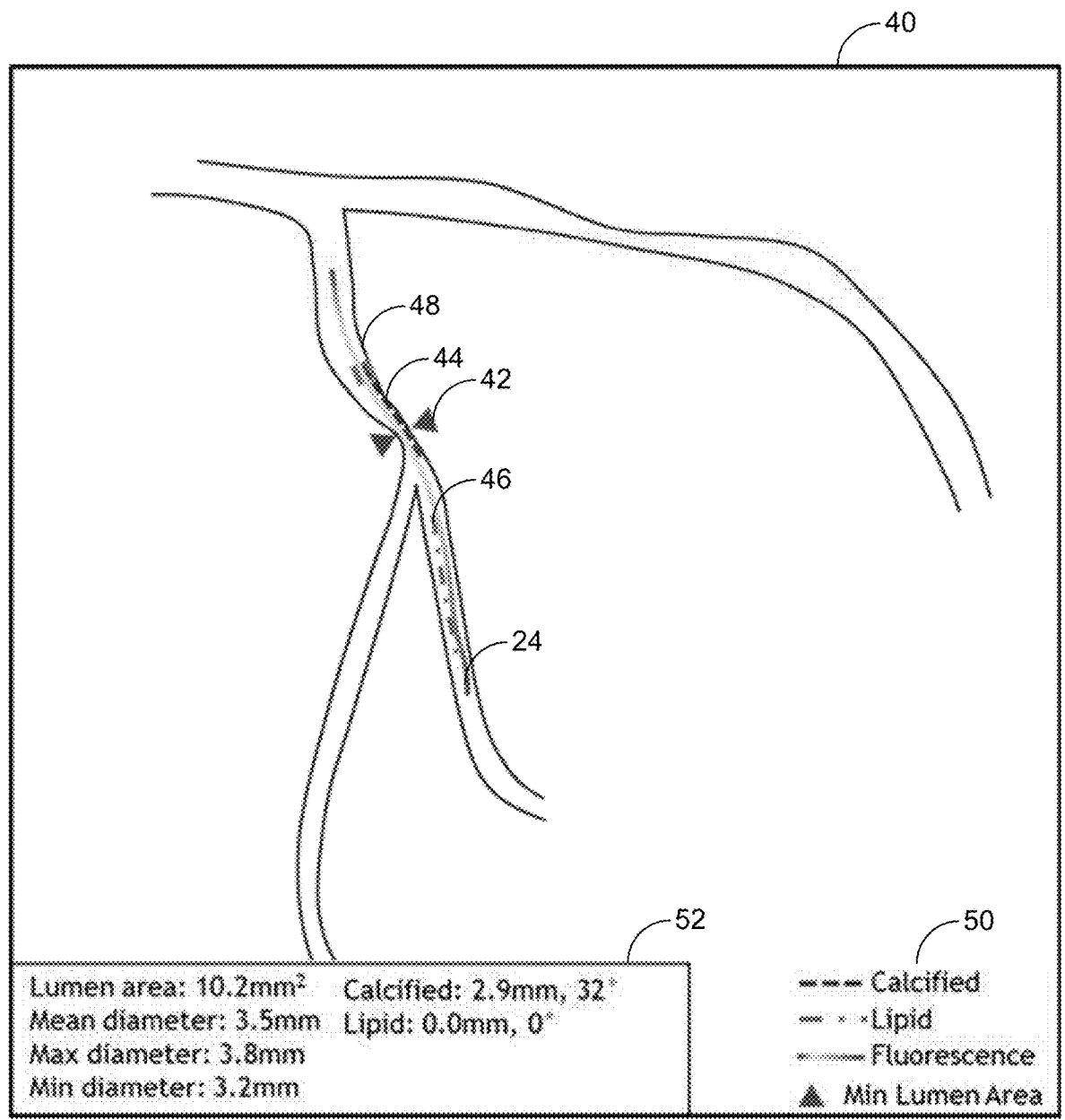
FIG. 19 is a diagram illustrating a graphical user interface at a percutaneous coronary intervention planning stage when intravascular imaging occurs at a region that includes bifurcation in accordance with one or more aspects of the present disclosure.

If an intravascular imaging pullback occurs in a region that includes bifurcation(s), the system creates an interpolated line that mimics lumen edge at the bifurcation location based on the co-registration path and overlay any qualitative information in the same manner using the interpolated line as the lumen edge over the bifurcation. One example method to create the interpolated line is that the processor measures the distance between the co-registration path and the lumen edge before and after the bifurcation and creates a line that is apart from the co-registration path with the measured distance within the bifurcation region. The interpolated line should be connected to the detected lumen edge in a pixelated space before and after the bifurcation. FIG. 19 shows an example GUI at pre-PCI stage.

In another embodiment, all the detected qualitative information can be displayed by overlaying on a live angiography image received from an angiography system including an X-ray source, an X-ray detector and a contrast agent injection device, each being operated simultaneously to perform angiographic imaging. The live angiography image may be transmitted by the angiography system, via a cable connecting the intravascular imaging system, such as MM-OCT system 02 with the angiography system. In one example, to match the location between the angiography image that is acquired during the intravascular imaging pullback and the live angiography image, an aligning matrix is created by detecting features that can be found and are corresponding in both images. Then, the processor places qualitative information at the aligned co-registration location on the live angiography image via the aligning matrix. If a user helps the processor, for example, by placing one or multiple user input(s) to identify the targeted vessel in the angiography image that is acquired during intravascular imaging pullback and if the acquisition angle of the live angiography image has not changed, the user input(s) can be used to identify the targeted vessel in the live angiography image.

In another embodiment, all the detected qualitative information can be displayed by overlaying on the most-recently acquired angiography image. If a user prefers, the information can be overlaid only on the last frame or all the frames in the most-recently acquired angiography image. This helps a user to refer to the qualitative information that is acquired previously to the angiography image. If it is just after acquiring the intravascular image with the simultaneous angiography image, this angiography image is the image that is referred to in this embodiment. If there is another angiography image that is acquired after intravascular imaging pullback, and if a user would like to see the previously detected and evaluated qualitative information, the qualitative information can be displayed on that angiography image in a similar manner described above. The process to display the qualitative information on the last frame, in one example, is initiated when the intravascular imaging system detects the signal that a user finishes acquiring the angiography image, e.g., freeing the pedal of the angiography system that controls X-ray irradiation. The signal may be transmitted via the cable connecting the intravascular imaging system and the angiography system acquiring the angiography image. The cable may also be used for transmitting the angiography image from the X-ray imaging modality to the intravascular imaging system. The overlaid location can be determined in the similar method that is used to overlay on the live angiography image.

Figure 20:
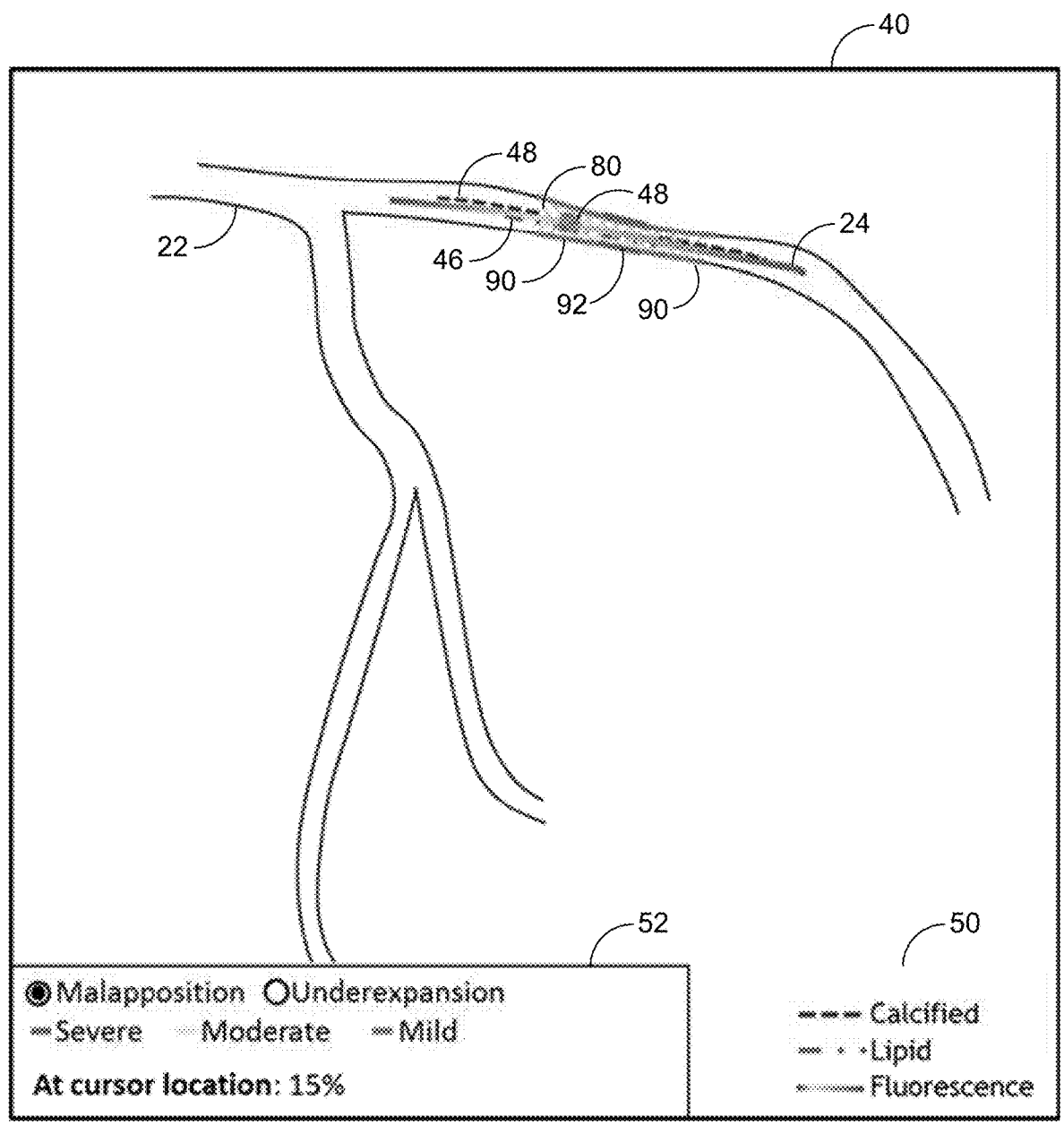
FIG. 20 is a diagram illustrating a graphical user interface at post-percutaneous coronary intervention procedure in accordance with one or more aspects of the present disclosure.

In another embodiment, at post-PCI stage, if a user prefers, the image processor can display all the qualitative information, which are listed in Table 1, on a post-PCI angiography image. FIG. 20 shows one example of the GUI that displays all the qualitative information. The post-PCI angiography image can be the image that is simultaneously acquired to intravascular imaging pullback, the live image that is acquired after stent is implanted, or the most-recently acquired angiography image at post-PCI stage.

In another embodiment, at post-PCI stage, the processor may generate a new type of qualitative information for a physician to navigate a further interventional procedure during step S202 in FIG. 10. One such example includes information to guide post-dilation. The goal of stenting is to make sure that the entire stent is sufficiently expanded and well-apposed. To achieve this goal, the implanted stent may be post-dilated. This information can be displayed as three levels, a first level 1 (Caution), second level 2 (Insufficient), or third level 3 (Sufficient), or binary, such as 1 (Needs post-dilation) or 0 (No need). This type of information may be overlaid within $(x_n\_edge1, y_n\_edge1)$ and $(x_n\_edge2, y_n\_edge2)$ on n_line, or on the lumen edge, i.e., $(x_n\_edge1, y_n\_edge1)$ or $(x_n\_edge2, y_n\_edge2)$. The same restriction and the interpolation steps are applied between the adjacent intravascular image frames.

The overlaid location can be set as a default by the system or can be selected by a user based on the user's preference.

As a default, the system can set to overlay the information that is related to a vessel itself, i.e., n_plaque_i, and n_NIR (A)F, within ($x_n$_edge1, $y_n$_edge1) and ($x_n$_edge2, $y_n$_edge2) on n_line, and the information that is related to an implanted device, such as a stent, i.e., n_stent_expan_serverity, n_stent_malap_severit, and n_stent_dissec, on the lumen edge, i.e., ($x_n$_edge1, $y_n$_edge1) or ($x_n$_edge2, $y_n$_edge2). The same restriction and the interpolation steps are applied between the adjacent intravascular image frames.

In another embodiment, if there are multiple types of the qualitative information to be displayed, the different type of qualitative information can be displayed on each lumen edge, i.e., ($x_n$_edge1, $y_n$_edge1) or ($x_n$_edge2, $y_n$_edge2). The overlaid location can be pre-set by the processor or can be modified by a user. If a user prefers, even if only one type of qualitative information is displayed, the information can be overlaid at one edge, i.e., either ($x_n$_edge1, $y_n$_edge1) or ($x_n$_edge2, $y_n$_edge2). The same interpolation steps are applied between the adjacent intravascular image frames.

In another embodiment, if there are more types of qualitative information than the available overlaid location although displaying different type of information overlaying on each lumen edge, the processor can display the qualitative information outside of the lumen edge if a user prefers. The overlaid location outside of the lumen edge should be separated from lumen edge in pixelated dimension.

In another embodiment, the processor can determine the maximum number to display and overlay the quantitative information based on location of the intravascular imaging pullback in a coronary artery tree and size of the vessel. If the pullback location is relatively distal side of the coronary artery tree and there is/are no side branch(es) or only small side branch(es), the outside of the detected lumen edge can be counted as one of possible overlaid location. The location of the pullback can be automatically determined by the processor or can be entered by a user. Within the vessel, the size of the vessel at minimum diameter in the pixelated space is a factor to determine the number of overlaid location. A user also can select the maximum number of the overlaid location before and/or during the procedure. If the user-selected number exceeds the processor-determined number, the system will select the processor-determined number and can display a notification to let a user know.

Figure 21:
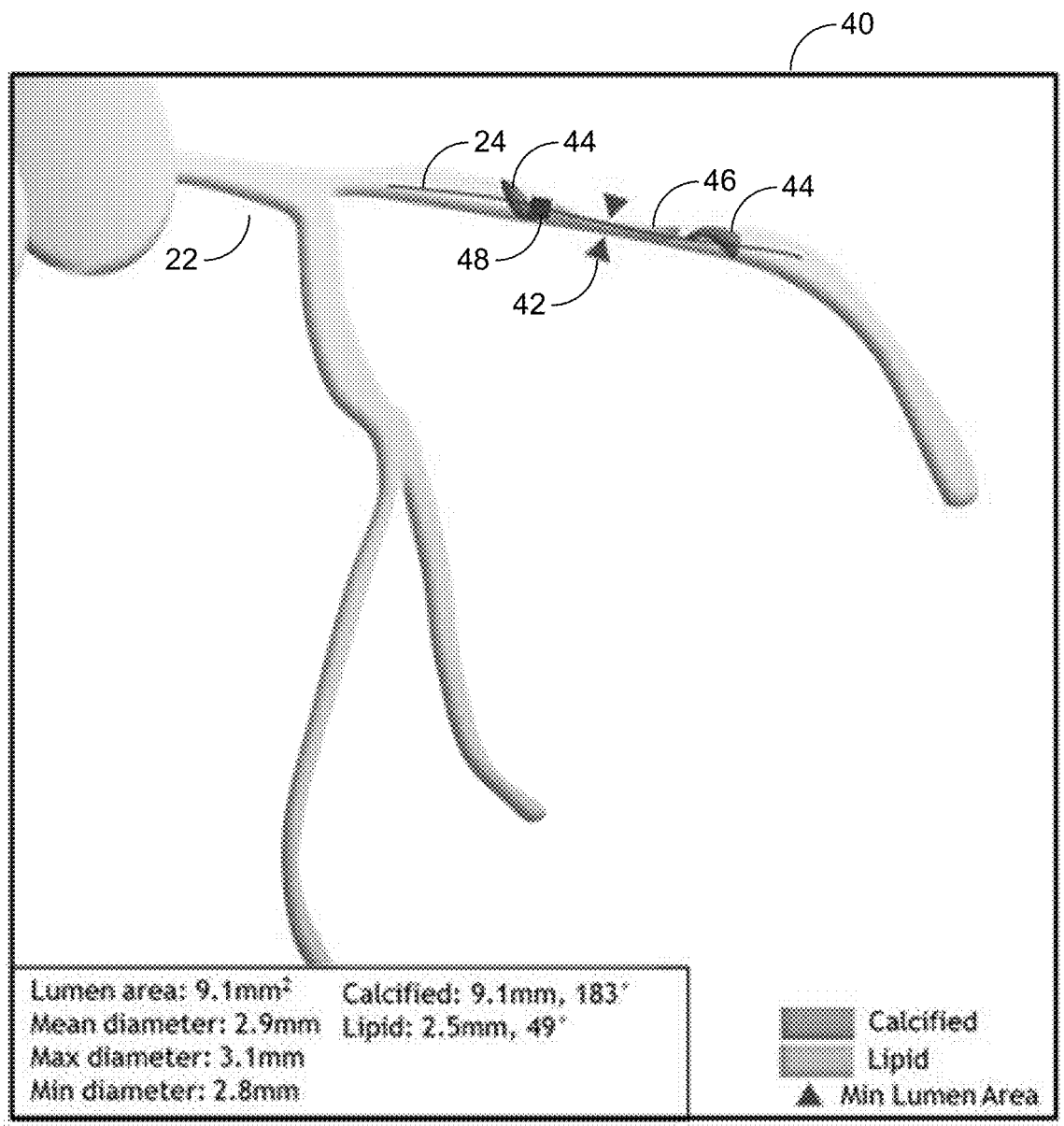
FIG. 21 is a diagram illustrating a graphical user interface with a three-dimensional rendering of the anatomical image in accordance with one or more aspects of the present disclosure.

FIG. 21 shows a diagram of the GUI 40 where the anatomical image of the coronary artery 22 is not an angiography image. In the previous FIGS. of the present disclosure, coronary angiography represented the primary imaging modality for PCI, but other imaging modalities, such as computed tomography (CT), CT angiography, magnetic resonance imaging (MRI), and cardiac MRI can be used for understanding the anatomy of the targeted coronary artery/arteries. If one or multiple of these imaging modalities is used instead of coronary angiography, a 3D structure of the targeting coronary artery is first reconstructed. This reconstructed structure is displayed on the monitor as shown in the GUI 40 of FIG. 21. Then, the 3D structure is co-registered with the intravascular image frames, so that the qualitative and quantitative information from the intravascular image frames can be overlaid on the displayed reconstructed 3D structure. The monitor can display a 2D image, like a coronary angiography image, that is projected from the 3D reconstructed structure.

The overlaid location is determined based on co-registration in a similar manner described above. The method to overlay the information from intravascular imaging may be different. When the reconstructed 3D structure is used, the quantitative information can be displayed in 3D by placing the information from the intravascular imaging on the surface of the reconstructed structure as shown in FIG. 21. If a user wants to see only the qualitative information, this information can be overlaid within the 3D structure at the corresponding co-registration location. If a user prefers 2D projected image, both the qualitative information and the quantitative information can be displayed in a similar manner to that when an angiography image is displayed in the GUI 40.

The zoom-in feature is also available in case when a user prefers to see the ROI path 24 in greater detail. If a 3D reconstructed structure is used as the basic displayed view, the zoom-in feature can provide an enlarged view of the ROI path 24 in an additional view that is overlapped on the original view. If a 2D projected image is used as the basic displayed view, the zoom-in feature can provide either an enlarged view of the ROI path 24 or the visualized version of the quantitative information of the ROI path 24 in the additional view.

Figure 22:
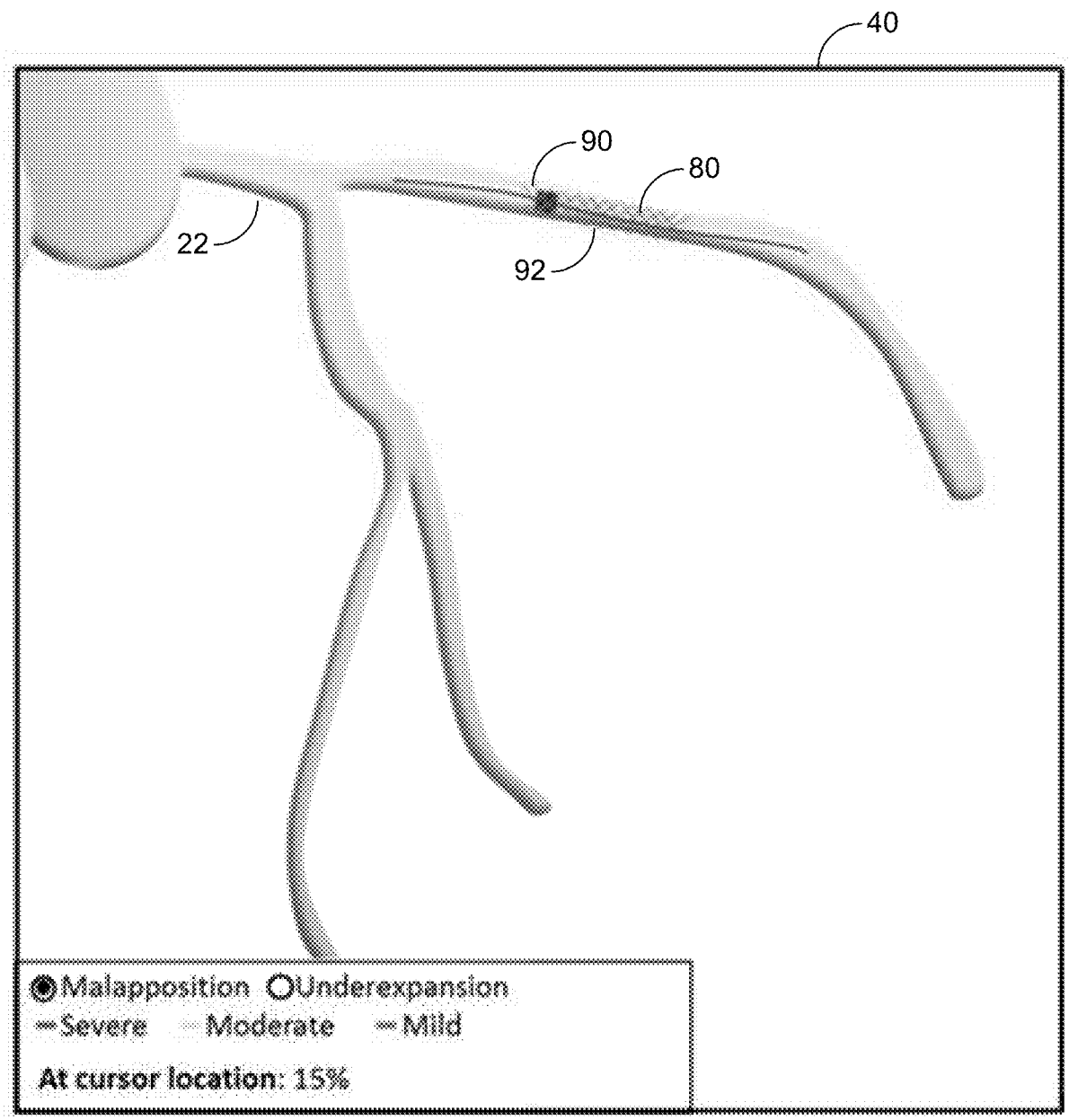
FIG. 22 is a diagram illustrating a graphical user interface with a three-dimensional rendering of the anatomical image for visualizing a post-stenting stage in accordance with one or more aspects of the present disclosure.

FIG. 22 shows a diagram of the GUI 40 at a post-stenting stage when an angiography image is not used as the anatomical image of the coronary artery 22. The user has selected to view stent malapposition in the GUI 40. The indicator for the stent structure 80 is overlaid within the coronary artery 22 with different shaded indicators representing the severity of the stent malapposition. Indicator 90 represents mild stent malapposition and indicator 92 represents severe stent malapposition.

Figure 23:
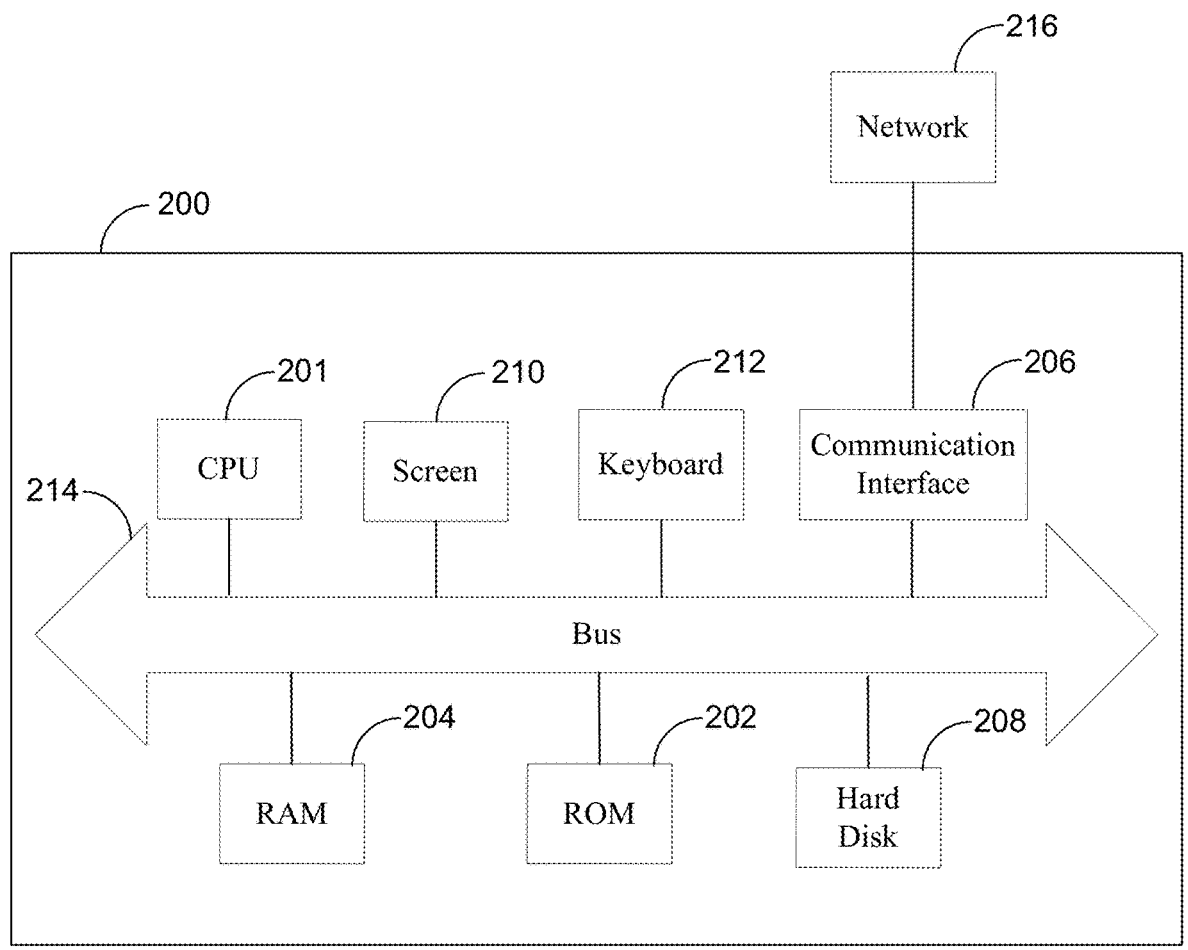
FIG. 23 is a schematic diagram of an embodiment of a computer that may be used with one or more embodiments of a graphical user interface in accordance with one or more aspects of the present disclosure.

FIG. 23 is an exemplary block diagram of a hardware configuration of the computer 08 of FIG. 1. However, the computer 200 may be implemented in an imaging system other than the MM-OCT system 02 of FIG. 1. The computer 200 include a central processing unit ("CPU") 201, a ROM 202, a RAM 204, a communication interface 206, a hard disk (and/or other storage device) 208, a display interface 210, a keyboard (or input interface; may also include a mouse or other input device in addition to the keyboard) 212 and a BUS or other connection lines (e.g., connection line 214) between one or more of the aforementioned components as shown in FIG. 2. The computer 200 may include one or more combinations of the other aforementioned components. The CPU 201 is configured to read and perform computer-executable instructions stored in a storage medium. The computer-executable instructions may include those for the performance of the methods and/or calculations described herein. The computer 200 may include one or more additional processors in addition to CPU 201, and such processors, including the CPU 201, may be used for acquiring information from an intravascular imaging system, overlaying the acquired information onto an anatomical image frame obtained from an anatomical imaging system and displaying the anatomical image with the overlaid information. The computer 200 may further include one or more processors connected via a network connection (e.g., via network 216). The CPU 201 and any additional processor being used by the computer 200 may be located in the same telecom network or in different telecom networks.

The I/O or communication interface 206 provides communication interfaces to input and output devices, which may include the two light sources 06, a communication cable and a network (either wired or wireless), a keyboard 212, a mouse, a touch screen or monitor 04.

Any methods and/or data of the present disclosure, such as the methods for displaying a GUI of an anatomical image as discussed herein, may be stored on a computer-readable storage medium. A computer-readable and/or writable storage medium used commonly, such as, but not limited to, one or more of a hard disk (e.g., the hard disk 108, a magnetic disk, etc.), a flash memory, a CD, an optical disc (e.g., a compact disc ("CD") a digital versatile disc ("DVD"), a Blu-Ray™ disc, etc.), a magneto-optical disk, a random-access memory ("RAM") (such as the RAM 104), a DRAM, a read only memory ("ROM"), a storage of distributed computing systems, a memory card, or the like (e.g., other semiconductor memory, such as, but not limited to, a non-volatile memory card, a solid state drive, SRAM, etc.), an optional combination thereof, a server/database, etc. may be used to cause a processor, such as, the processor or CPU 201 of the aforementioned computer 200 to perform the steps of the methods disclosed herein. The computer-readable storage medium may be a non-transitory computer-readable medium, and/or the computer-readable medium may comprise all computer-readable media, with the sole exception being a transitory, propagating signal. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

The above described devices, systems, and methods can be implemented by supplying one or more computer-readable media having stored therein computer-executable instructions for realizing the above described operations to one or more computer devices that are configured to read the computer-executable instructions and execute them. In this case, the system or devices perform the operations of the above-described embodiments when executing the computer-executable instructions. Also, an operating system on the one or more systems or devices may implement the operations of the above described embodiments. Thus, the computer-executable instructions or the one or more computer-readable media storing the computer-executable instructions or the one or more computer-readable media storing the computer-executable instructions thereon constitute an embodiment.

While the above disclosure describes certain illustrative embodiments, the present disclosure is not limited to the above-described embodiments, and the following claims include various modifications and equivalent arrangements within their scope.

What is claimed is:

1. A method for displaying an anatomical image of a coronary artery on a graphical user interface, the method comprising:
   acquiring the anatomical image of the coronary artery;
   acquiring a plurality of intravascular image frames of the coronary artery associated with the anatomical image at a plurality of acquisition locations;
   detecting qualitative information from the plurality of intravascular image frames;
   creating one or more indicator(s) from the qualitative information;
   determining a spatial relationship between the anatomical image and the plurality of acquisition locations of the plurality of intravascular image frames and generating a linear representation based on the spatial relationship;
   displaying the anatomical image of the coronary artery with the linear representation overlaid on the displayed anatomical image on a display device;
   overlaying the one or more indicator(s) representing at least one type of qualitative information on the anatomical image along the linear representation such that the one or more indicator(s) are located along, adjacent to, on, or in the coronary artery; and
   displaying information using one or more of two display modes,
   wherein a first display mode of the two display modes displays the anatomical image with the overlaid one or more indicator(s), the overlaid linear representation, and one or more values or a legend, without displaying an intravascular image based on one or more of the plurality of intravascular image frames, the one or more values or the legend defining the one or more indicator(s) and being displayed on the display device, and
   wherein a second display mode of the two display modes displays both one or more intravascular images based on one or more of the plurality of intravascular image frames and the anatomical image having the overlaid one or more indicator(s) and the overlaid linear representation, and the display device displays the one or more values or the legend.

2. The method of claim 1, wherein the qualitative information detected from the plurality of intravascular image frames include at least one of plaque morphology, thrombus, stent thrombus, stent apposition, stent malapposition, stent edge dissection, stent-strut coverage or detection, neointima formation, near-infrared auto fluorescence (NIRAF), plaque type, different geometric size or shape to define the corresponding indicator, information indicating that the qualitative information is fluorescence information, information regarding stent expansion or underexpansion, and tissue protrusion, and
   wherein the one or more values or the legend include qualitative information and/or quantitative information.

3. The method of claim 1, wherein the one or more indicator(s) comprise at least two different indicators that are overlaid on the anatomical image, wherein the two indicators have different types of qualitative information and wherein the at least two different indicators are positioned differently or at different locations in a radial direction of the coronary artery such that each of the at least two different indicators are distinguishable on the display of the display device.

4. The method of claim 1, wherein one or more of the following:
   (i) the one or more values or the legend include one or more of: the qualitative information and quantitative information, wherein the quantitative information include one or more of lumen area and diameter, a minimum lumen diameter value, a maximum lumen diameter value, a minimum lumen area, a mean lumen diameter, stent area and diameter, a minimum stent diameter value, a maximum stent diameter value, a distance between two indicators of the one or more indicator(s) or between two markers, stent malapposition distance, stent malapposition severity, stent underexpansion severity, plaque size or area, resorption rate of bio-absorbable stent, fractional flow reserve, cursor location, size and angle of a calcified plaque, size and angle of a lipid plaque, size and angle of fluorescence, and near-infrared autofluorescence (NIRAF) intensity and area; and (ii) the one or more values or the legend are overlaid or displayed on the anatomical image such that the one or more values or the legend do not cover the coronary artery or any other nearby anatomical feature(s).

5. The method of claim 1, wherein the linear representation is a line, and the line corresponds to an intravascular imaging pullback procedure from an intravascular imaging system.

6. The method of claim 1, wherein a user selects a type of qualitative information or a type of quantitative information to be overlaid.

7. The method of claim 1, wherein the one or more indicator(s) comprise a plurality of indicators that is overlaid on the anatomical image by including multiple longitudinal paths at different locations in a radial direction of the coronary artery.

8. The method of claim 1, wherein in the overlaying of the one or more indicator(s) step, the one or more indicator(s) is/are overlaid on the anatomical image in response to a receipt of a signal indicating that a user finishes acquiring an anatomical image at an X-ray imaging modality.

9. A non-transitory computer-readable storage medium storing a computer-readable program for causing a computer to executed the method according to claim 1.

10. A graphical user interface apparatus comprising:
a memory;
a processor coupled to the memory which executes the following:
    acquiring an anatomical image of a coronary artery;
    acquiring a plurality of intravascular image frames of the coronary artery associated with the anatomical image at a plurality of acquisition locations;
    detecting qualitative information from the plurality of intravascular image frames;
    creating one or more indicator(s) from the qualitative information;
    determining a spatial relationship between the anatomical image and the plurality of acquisition locations of the plurality of intravascular image frames and generating its linear representation based on the spatial relationship;
    displaying the anatomical image of the coronary artery with the linear representation overlaid on the displayed anatomical image on a display device;
    overlaying the one or more indicator(s) representing at least one type of qualitative information on the anatomical image along the linear representation such that the one or more indicator(s) are located along, adjacent to, on, or in the coronary artery; and
    displaying information using one or more of two display modes,
    wherein a first display mode of the two display modes displays the anatomical image with the overlaid one or more indicator(s), the overlaid linear representation, and one or more values or a legend, without displaying an intravascular image based on one or more of the plurality of intravascular image frames, the one or more values or the legend defining the one or more indicator(s) and being displayed on the display device, and
    wherein a second display mode of the two display modes displays both one or more intravascular images based on one or more of the plurality of intravascular image frames and the anatomical image having the overlaid one or more indicator(s) and the overlaid linear representation, and the display device displays the one or more values or the legend.

11. A method for processing a plurality of intravascular image frames, the method comprising:
an acquiring step for acquiring an anatomical image frame of a blood vessel;
an acquiring step for acquiring the plurality of intravascular image frames of the blood vessel associated with the anatomical image frame at a plurality of acquisition locations, wherein the plurality of acquisition locations of the plurality of intravascular image frames are visualized in the anatomical image frame;
a detecting step for detecting items of information of a predetermined type related to the blood vessel from the plurality of intravascular image frames; and
a displaying step for displaying one or more indicators representative of the detected items of information at corresponding locations inside, on, adjacent to, or along the blood vessel of the anatomical image frame, and for displaying information on a display device using one or more of two display modes,
wherein a first display mode of the two display modes displays the anatomical image frame with the displayed one or more indicators and one or more values or a legend, without displaying an intravascular image based on one or more of the plurality of intravascular image frames, the one or more values or the legend defining the one or more indicators and being displayed on the display device, and
wherein a second display mode of the two display modes displays both one or more intravascular images based on one or more of the plurality of intravascular image frames and the anatomical image frame having the displayed one or more indicators, and displays the one or more values or the legend.

12. The method of claim 11, wherein in the displaying step, the one or more indicators representative of the detected items of information are displayed inside, on, adjacent to, or along the blood vessel so that the one or more indicators are not overlaid on a tissue region outside the blood vessel of the anatomical image frame.

13. The method of claim 11, wherein the acquiring step further includes acquiring from a $1^{st}$ to $N^{th}$ intravascular image frames spatially arranged in this order where the $N^{th}$ intravascular image frame is greater than an $n^{th}$ intravascular image frame and the $n^{th}$ intravascular image frame is greater than 1, and
when the information of the predetermined type is not detected from the $n^{th}$ intravascular image frame, the information of the predetermined type is obtained based on at least one of the information detected from the $n^{th}-1$ intravascular image frame, and the information detected from the $n^{th}+1$ intravascular image frame.

14. The method of claim 11, wherein the detecting step further includes, when information to be displayed at a location in the anatomical image is not detected from an intravascular image frame, obtaining information of the predetermined type based on the detected information to be displayed at a neighboring location of the location in the anatomical image frame.

15. The method of claim 11, wherein the acquiring step further includes acquiring from a $1^{st}$ to $N^{th}$ intravascular image frames spatially arranged in this order where N is greater than an $n^{th}$ intravascular image frame and the $n^{th}$ intravascular image frame is greater than 1, and
when the information of the predetermined type is not detected from an $n(t)^{th}$ intravascular image frames, wherein t represents successive intravascular image frames and t is greater than 1, the one or more indicators at corresponding locations in the anatomical image frame are displayed.

16. The method of claim 11, wherein the acquiring step further includes acquiring from a $1^{st}$ to $N^{th}$ intravascular image frames spatially arranged in this order where the $N^{th}$ intravascular image frame is greater than an $n^{th}$ intravascular image frame and the $n^{th}$ intravascular image frame is greater than 1, and
when the information of the predetermined type is not detected from an $n(t)^{th}$ intravascular image frames, wherein t represents successive intravascular image frames and t is greater than 1, the one or more indicators at corresponding locations in the anatomical image frame are not displayed.

17. The method of claim 11, wherein in the displaying step, when information to be displayed at a predetermined number of successive locations in the anatomical image frame is not detected, the one or more indicators at corresponding locations in the anatomical image frame are not displayed.

18. The method of claim 11, further comprising:
detecting information of multiple predetermined types from each intravascular image frame from the plurality of intravascular image frames; and
setting a type of information to be displayed,
wherein the displaying step further includes displaying indicators representative of the detected information of the set type.

19. The method of claim 11, wherein in the acquiring step, it is determined that a stent is not deployed in at least a part of the blood vessel for the plurality of intravascular image frames acquired,
the detecting step further includes detecting the items of information of the predetermined type corresponding to the part of the blood vessel where the stent is not deployed, and
the displaying step further includes displaying the indicators representative of the detected items of information at corresponding locations inside, on, adjacent to, or along the part of the blood vessel in the anatomical image where the stent is not deployed.

20. The method of claim 19, further comprising:
processing pixel values of a tissue region of the blood vessel in the plurality of intravascular image frames to detect tissue information for each of the intravascular image frames; and
displaying the indicators representative of the detected tissue information.

21. The method of claim 1, wherein the one or more values and/or information in the legend are calculated from the intravascular image.

22. The method of claim 1, wherein the one or more values or the legend is displayed on or in the anatomical image.

23. The graphical user interface apparatus of claim 10, wherein the one or more values or the legend is displayed on or in the anatomical image.

24. The method of claim 11, wherein the one or more values or the legend is displayed on or in the anatomical image frame.

25. The method of claim 1, further comprising:
determining whether the one or more indicator(s) are to be overlaid within the coronary artery; and
in the event that the one or more indicator(s) are to be overlaid within the coronary artery, overlaying the one or more indicator(s) within the coronary artery, or, in the event that the one or more indicator(s) cannot be, or are not to be, overlaid within the coronary artery, overlaying the one or more indicator(s) on an edge or edges of the coronary artery, or adjacent to and/or outside of, the coronary artery.

26. The graphical user interface apparatus of claim 10, wherein the processor further operates to:
determine whether the one or more indicator(s) are to be overlaid within the coronary artery; and
in the event that the one or more indicator(s) are to be overlaid within the coronary artery, overlay the one or more indicator(s) within the coronary artery, or, in the event that the one or more indicator(s) cannot be, or are not to be, overlaid within the coronary artery, overlay the one or more indicator(s) on an edge or edges of the coronary artery, or adjacent to and/or outside of, the coronary artery.

27. The method of claim 11, further comprising:
determining whether the one or more indicators are to be overlaid within the blood vessel; and
in the event that the one or more indicators are to be overlaid within the blood vessel, overlaying the one or more indicators within the blood vessel, or, in the event that the one or more indicators cannot be, or are not to be, overlaid within the blood vessel, overlaying the one or more indicators on an edge or edges of the blood vessel, or adjacent to and/or outside of, the blood vessel.

28. The graphical user interface apparatus of claim 10, wherein one or more of the following:
(i) the one or more values or the legend include one or more of: the qualitative information and quantitative information, wherein the quantitative information include one or more of lumen area and diameter, a minimum lumen diameter value, a maximum lumen diameter value, a minimum lumen area, a mean lumen diameter, stent area and diameter, a minimum stent diameter value, a maximum stent diameter value, a distance between two indicators of the one or more indicator(s) or between two markers, stent malapposition distance, stent malapposition severity, stent underexpansion severity, plaque size or area, resorption rate of bio-absorbable stent, fractional flow reserve, cursor location, size and angle of a calcified plaque, size and angle of a lipid plaque, size and angle of fluorescence, and near-infrared autofluorescence (NIRAF) intensity and area, and wherein the qualitative information detected from the plurality of intravascular image frames include at least one of plaque morphology, thrombus, stent thrombus, stent apposition, stent malapposition, stent edge dissection, stent-strut coverage or detection, neointima formation, near-infrared auto fluorescence (NIRAF), plaque type, different geometric size or shape to define the corresponding indicator, information indicating that the qualitative information is fluorescence information, information regarding stent expansion or underexpansion, and tissue protrusion; and (ii) the one or more values or the legend are overlaid or displayed on the anatomical image such that the one or more values or the legend do not cover the coronary artery or any other nearby anatomical feature(s).

29. The method of claim 11, wherein one or more of the following:
   (i) the one or more values or the legend include one or more of: the qualitative information and quantitative information, wherein the quantitative information include one or more of lumen area and diameter, a minimum lumen diameter value, a maximum lumen diameter value, a minimum lumen area, a mean lumen diameter, stent area and diameter, a minimum stent diameter value, a maximum stent diameter value, a distance between two indicators of the one or more indicator(s) or between two markers, stent malapposition distance, stent malapposition severity, stent underexpansion severity, plaque size or area, resorption rate of bio-absorbable stent, fractional flow reserve, cursor location, size and angle of a calcified plaque, size and angle of a lipid plaque, size and angle of fluorescence, and near-infrared autofluorescence (NIRAF) intensity and area, and wherein the qualitative information detected from the plurality of intravascular image frames include at least one of plaque morphology, thrombus, stent thrombus, stent apposition, stent malapposition, stent edge dissection, stent-strut coverage or detection, neointima formation, near-infrared auto fluorescence (NIRAF), plaque type, different geometric size or shape to define the corresponding indicator, information indicating that the qualitative information is fluorescence information, information regarding stent expansion or underexpansion, and tissue protrusion; and
   (ii) the one or more values or the legend are overlaid or displayed on the anatomical image frame such that the one or more values or the legend do not cover the blood vessel or any other nearby anatomical feature(s).

* * * * *